US005827694A

United States Patent [19]

Capon et al.

[11] Patent Number: 5,827,694

[45] Date of Patent: Oct. 27, 1998

[54] DNA ENCODING NON-HUMAN ANIMAL INTERFERONS, VECTORS AND HOSTS THEREFOR, AND RECOMBINANT PRODUCTION OF IFN POLYPEPTIDES

[75] Inventors: Daniel J. Capon, San Mateo; David V. Goeddel, Hillsborough, both of Calif.

[73] Assignee: Genentech, Inc., South San Francisco, Calif.

[21] Appl. No.: 446,171

[22] Filed: May 19, 1995

Related U.S. Application Data

[62] Division of Ser. No. 949,327, Sep. 21, 1992, which is a continuation of Ser. No. 749,371, Aug. 23, 1991, abandoned, which is a continuation of Ser. No. 104,461, Oct. 2, 1987, abandoned, which is a continuation-in-part of Ser. No. 438,128, Nov. 1, 1982, abandoned, which is a continuation-in-part of Ser. No. 395,298, Mar. 8, 1982, abandoned.

[51] Int. Cl.[6] .......................... C12N 15/20; C12N 15/21; C12N 15/22; C12N 15/23

[52] U.S. Cl. .................................... 435/69.51; 536/23.52; 536/23.4; 435/320.1; 435/325; 435/252.3; 435/252.33

[58] Field of Search ............................... 536/23.52, 23.4; 435/69.51, 320.1, 240.2, 252.3, 252.33, 325

[56] References Cited

U.S. PATENT DOCUMENTS

| | | |
|---|---|---|
| 3,970,749 | 7/1976 | Baugh . |
| 4,262,090 | 4/1981 | Colby . |
| 4,289,690 | 9/1981 | Pestka . |
| 4,332,892 | 6/1982 | Ptashne . |
| 4,468,464 | 8/1984 | Cohen . |

FOREIGN PATENT DOCUMENTS

| | | |
|---|---|---|
| 018218 | 4/1980 | European Pat. Off. . |
| 034306 | 2/1981 | European Pat. Off. . |
| 034307 | 2/1981 | European Pat. Off. . |
| 028033 | 5/1981 | European Pat. Off. . |
| 042246 | 6/1981 | European Pat. Off. . |
| 043980 | 6/1981 | European Pat. Off. . |
| 032134 | 7/1981 | European Pat. Off. . |
| 2063882 | 11/1980 | United Kingdom . |
| 2069504 | 2/1981 | United Kingdom . |
| 2079291 | 7/1981 | United Kingdom . |
| 2098996 | 9/1981 | United Kingdom . |
| 2107718 | 10/1982 | United Kingdom . |
| WO 80/02375 | 11/1980 | WIPO . |
| WO 82/00588 | 3/1982 | WIPO . |

OTHER PUBLICATIONS

Ahl and Rump, "Assay of bovine interferons in cultures of the porcine cell line IB–RS–2" *Infection and Immunity* 14(3):603–606 (1976).

Babiuk and Rouse, "Bovine type II interferon: activity in heterologous cells" *Intervirology* 8(4):250–256 (1977).

Babiuk and Rouse, "Immune interferon production by lymphoid cells: role in the inhibition of herpesviruses" *Infection and Immunity* 13(6):1567–1578 (1976).

Blalock et al., "Purified human immune interferon has more potent anticellular ativity than fibroblast or leukocyte interferon" *Cellular Immunology* 49:390–394 (1980).

Bloom, "Interferons and the immune system" *Nature* 284(5757):593–595 (1980).

Booner et al., "Reduction in the rate of DNA reassociation by sequence divergence" *J. Mol. Biol.* 81:123–135 (1973).

Carter et al., "Purified human fibroblast interferon in vivo: skin reactions and effect on bone marrow precursor cells" *Cancer Letters* 7(5):243–249 (1979).

Carter W., "Glycosylation, intraspecies molecular heterogeneity and trans–species activity of mammalian interferons" *Life Sciences* 25(9):717–728 (1979).

Carter W., "Mechanisms of cross–species activity of mammalian interferons" *Pharmacology & Therapeutics* 7(2):245–252 (1979).

Carter W. and Johnson, "Induction and production of interferon with porcine, bovine, and equine leukocytes" *Methods in Enzymology* 78(Pt. A):48–54 (1981).

Carter W. et al., "Porcine leukocyte interferon and antiviral activity in human cells" *Molecular Pharmacology* 15(3):685–690 (1979).

Chang et al., "Phenotypic Expression in *E. coli* of a DNA Sequence Coding for Mouse Dihydrofolate Reductase" *Nature* 275:617–624 (1978).

Crane et al., "Inhibition of murine osteogenic sarcomas by treatment with type I or type II interferon" *Journal of the National Cancer Institute* 61(3):871–874 (1978).

Fleischmann et al., "Potentiation of interferon activity by mixed preparations of fibroblast and immune interferon" *Infection and Immunity* 26(1):248–253 (1979).

Fraser and Bruce, "Chicken ovalbumin is synthesized and secreted by *Escherichia coli*" *Proc. Natl. Acad. Sci. USA* 75(12):5936–5940 (1978).

Fulton and Rosenquist, "In vitro interferon production by bovine tissues: induction with infectious bovine rhinotracheitis virus" *American Journal of Veterinary Research* 37(12):1497–1502 (1976).

Goeddel et al., "Direct Expression in *Escherichia coli* of a DNA Sequence Coding for Human Growth Hormone" *Nature* 281(5732):544–548 (1979).

Goeddel et al., "Human leukocyte interferon produced by *E. coli* is biologically active" *Nature* 287(5781):411–416 (1980).

Goeddel et al., "The structure of eight distinct cloned human leukocyte interferon cDNAs" *Nature* 290(5801):20–26 (1981).

(List continued on next page.)

*Primary Examiner*—David L. Fitzgerald
*Attorney, Agent, or Firm*—Ginger R. Dreger; Richard B. Love

[57] ABSTRACT

Distinct α-, β- and γ-interferon genes from various animal species have been identified, cloned and expressed to produce the corresponding non-human animal interferon proteins. Specifically disclosed are interferons of bovine, porcine, feline and rabbit origin.

21 Claims, 33 Drawing Sheets

OTHER PUBLICATIONS

Goeddel et al., "Synthesis of Human Fibroblast Interferon by *E. coli*" *Nucleic Acids Research* 8(18):4057–4074 (1980).
Gresser et al., "Pronounced antiviral activity of human interferon on bovine and porcine cells" *Nature* 251(5475):543–545 (1974).
Gutterman et al., "Leukocyte interferon–induced tumor regression in human metastatic breast cancer, multiple myeloma, and malignant lymphoma" *Annals of Internal Medicine* 93(3):399–406 (1980).
Itakura et al., "Expression in *Escherichia coli* of a Chemically Synthesized Gene for the Hormone Somatostatin" *Science* 198:1056–1063 (1977).
Kato, K. et al., "CD48 is a counter–receptor for mouse CD2 and is involved in T cell activation" *Journal of Experimental Medicine* 176:1241–1249 (1992).
Martial et al., "Human Growth Hormone: Complementary DNA Cloning and Expression in Bacteria" *Science* 205:602–607 (1979).
McGrath & Levinson, "Bacterial expression of an enzymatically active protein encoded by RSV src gene" *Nature* 295:423–425 (1982).
McKnight, A.J. et al., "Sequence of a rat MHC class II–associated invariant chain cDNA clone containing a 64 amino acid thyroglobulin–like domain" *Nucleic Acids Research* 17(10):3983–3984 (1989).
Mercereau–Puijalon et al., "Synthesis of an ovalbumin–like protein by *Escherichia coli* K12 harbouring a recombinant plasmid" *Nature* 275(5680):505–510 (1978).
Miozzari and Yanofsky, "Translation of the leader region of the *Escherichia coli* tryptophan operon" *Journal of Bacteriology* 133(3):1457–1466 (1978).
Nagahari, "Deletion plasmids from transformants of Pseudomonas aeruginosa trp cells with the RSF1010–trp hybrid plasmid and high levels of enzyme activity from the gene on the plasmid" *Journal of Bacteriology* 136(1):312–317 (1978).
Nagata et al., "Synthesis in *E. coli* of a polypeptide with humam leukocyte interferon activity" *Nature* 284(5754):316–320 (1980).
Nakamura et al., "Relative contribution of CD2 and LFA–1 to murine T and natural killer cell functions" *J. Immunol.* 145(11):3628–3634 (1990).
Nishida, Y. et al., "Cloning of human immunoglobulin ϵ chain genes: evidence for multiple $C_\epsilon$ genes" *Proc. Natl. Acad. Sci.* 79:3833–3837 (1982).
Ohmann et al., "Effect of recombinant DNA–produced bovine interferon alpha (BoIFN–alpha 1) on the interaction between bovine alveolar macrophages and bovine herpesvirus type 1" *Journal of General Virology* 65 (Pt. 9):1487–1495 (1984).
Orlova et al., "Translation of messenger–RNA for interferon by bacterial cells and properties of interferon obtained" *Acta Biologica et Medica Germanica* 38(5–6):759–763 (1979).
Petterson et al. *Expression of Eukaryotic Viral & Cellular Genes* Academic Press pp. 295–303 (1981).
Remaut et al., "Plasmid vectors for high–efficiency expression controlled by the pL promotor of coliphage λ" *Gene* 15(1):81–93 (1981).
Rinaldo et al., "Fetal and adult bovine interferon production during bovine viral diarrhea virus infection" *Infection and Immunity* 14(3):660–666 (1976).
Rodriguez et al. *Promoters: Structure and Function* , Praeger Publ. pp. 452–461 (1982).
Rubin and Gupta, "Differential efficacies of human type I and type II interferons as antiviral and antiproliferative agents" *Proc. Natl. Acad. Sci. USA* 77(10):5928–5932 (1980).
Rutschmann & Karjalainen, "Mouse LFA–3 studied with chimeric soluable CD2 shows preferential expression on lymphoid cells" *European Journal of Immunology* 21:1379–1384 (1991).
Seeburg et al., "Synthesis of growth hormone by bacteria" *Nature* 276(5690):795–798 (1978).
Seed B., "An LFA–3 cDNA encodes a phospholipid–linked membrane protein homologous to its receptor CD2" *Nature* 329:840–842 (1987).
Shaw et al., "Structure and expression of cloned murine IFN–α genes" *Nucleic Acids Research* 11(3):555:573 (1983).
Skup et al., "Molecular cloning of partial cDNA copies of two distinct mouse IFN–β mRNAs" *Nucleic Acids Research* 10(10):3069–3084 (1982).
Sonnenfeld et al., "Time and dosage dependence of immunoenhancement by murine type II interferon preparations" *Cellular Immunology* 40(2):285–293 (1978).
Taniguchi et al., "Partial characterization of gamma (immune) interferon mRNA extracted from human lymphocytes" *Proc. Natl. Acad. Sci. USA* 78(6):3469–3472 (1981).
Todd et al., "Interferon in nasal secretions and sera of calves after intranasal administration of avirulent infectious bovine rhinotracheitis virus: association of interferon in nasal secretions with early resistance to challenge with virulent virus" *Infection and Immunity* 5(5):699–706 (1972).
Torma E. and Paucker K., "Purification and characterization of human leukocyte interferon components" *Journal of Biological Chemistry* 251(16):4810–4816 (1976).
Tovey et al., "Antiviral activity of bovine interferons on primate cells" *Journal of General Virology* 36(2):341–344 (1977).
Ullrich et al., "The structure and expression of the insulin gene" *International Congress Series* 467:20–26 (1979).
Velan et al., "Bovine interferon alpha gene. Structure and expression" *Journal of Biological Chemistry* 260(9):5498–5504 (1985).
Villa–Komaroff et al., "A bacterial clone synthesizing proinsuln" *Proc. Natl. Acad. Sci. USA* 75(8):3727–3731 (1978).
Word, C. et al., "The human immunoglobulin Cμ–Cδ locus: complete nucleotide sequence and structural analysis" *International Immunity* 1(3):296–309 (1989).
Yabrov, "Interferon: A broad–spectrum anti–viral agent" *Interferon and Nonspecific Resistance*, Human Sciences Press, Chapter 1, pp. 25–28 (1980).
Yelverton et al., "Bacterial synthesis of a novel human leukocyte interferon" *Nucleic Acids Research* 9(3):731–741 (1981).
Yip Y.K. et al., "Partial purification and characterization of human gamma (immune) interferon" *Proc. Natl. Acad. Sci. USA* 78(3):1601–1605 (1981).
Zarling et al., "Activation of human natural killer cells cytotoxic for human leukemia cells by purified interferon" *Journal of Immunology* 123(1):63–70 (1979).

```
GGATCCACAGCATAAATGTGTTGTCACAATTTCACGGTGGGGGTAATTAGGAAAAAAAAAATCTCAGAAGAACTGTCAATAGGGGAAGGGGGGCAATAATGAAAACAACGTTTGCGAA
                                                50                                                  100

ATGCTGTCCTAACCCATTTGAAGAGTACAAACTGAAAAACAAAAACAAAAGTAGAAAGCAAGAGGGAACTTTCAGAAAATGGAAACCATGGACTCCTATTTAAGACACAGACCTGAAGG
                            150                                                  200

                                                                                      S1                                 S10
                                                                                      met ala pro ala trp ser leu leu leu ala
AAGGTCTTCAGAGAACCTAGAAAGCAGGTTCACAGAGTCACCCACCGCCCCAGGCCACAAGCATCTTCAAGGTCCCCG        ATG GCC CCA GCC TGG TCC CTC CTC CTG GCT
          250                                                 300

                                    S20         S23 1                               10
leu leu leu leu ser cys asn ala ile cys ser leu gly CYS HIS LEU PRO HIS SER HIS SER LEU ALA LYS ARG ARG VAL LEU THR LEU
CTG CTG CTG CTC AGC TGC AAC GCC ATC TGC TCT CTG GGC TGC CAC CTG CCT CAC TCC CAC AGC CTG GCC AAG AGG AGA GTC CTG ACA CTC
  350                                                             400

        20                                      30                                      40
LEU ARG GLN LEU ARG ARG VAL SER PRO SER SER CYS LEU GLN ASP ARG ASN ASP PHE ALA PHE PRO GLN GLU ALA LEU GLY GLY SER GLN
CTG CGA CAA CTG AGG AGG GTC TCC CCT TCC TCC TGC CTG CAG GAC AGA AAT GAC TTC GCA TTC CCC CAG GAG GCG CTG GGT GGC AGC CAG
               450                                                                 500

        50                                      60                                      70
LEU GLN LYS ALA GLN ALA ILE SER VAL LEU HIS GLU VAL THR GLN HIS THR PHE GLN LEU PHE SER THR GLU GLY SER ALA ALA VAL TRP
TTG CAG AAG GCT CAA GCC ATC TCT GTA CTC CAC GAG GTG ACC CAA CAC ACC TTC CAG CTT TTC AGC ACA GAG GGC TCG GCC GCT GTG TGG
                            550                                                                 600
```

FIG. 3A-1

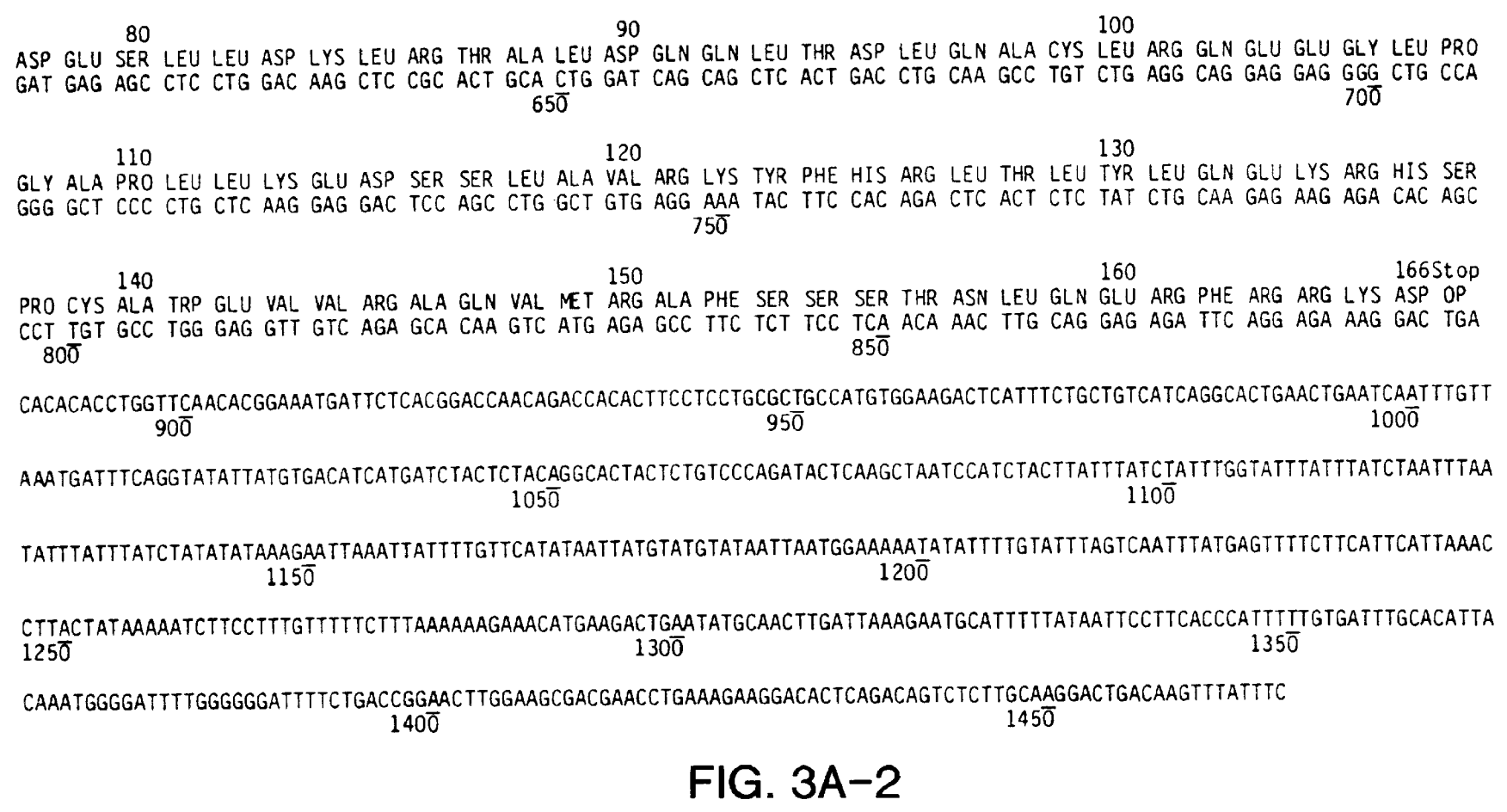

```
        80                                                90                                                100
ASP GLU SER LEU LEU ASP LYS LEU ARG THR ALA LEU ASP GLN GLN LEU THR ASP LEU GLN ALA CYS LEU ARG GLN GLU GLU GLY LEU PRO
GAT GAG AGC CTC CTG GAC AAG CTC CGC ACT GCA CTG GAT CAG CAG CTC ACT GAC CTG CAA GCC TGT CTG AGG CAG GAG GAG GGG CTG CCA
                                          650                                                                700

        110                                               120                                               130
GLY ALA PRO LEU LEU LYS GLU ASP SER SER LEU ALA VAL ARG LYS TYR PHE HIS ARG LEU THR LEU TYR LEU GLN GLU LYS ARG HIS SER
GGG GCT CCC CTG CTC AAG GAG GAC TCC AGC CTG GCT GTG AGG AAA TAC TTC CAC AGA CTC ACT CTC TAT CTG CAA GAG AAG AGA CAC AGC
                                                            750

        140                                               150                                               160                     166Stop
PRO CYS ALA TRP GLU VAL VAL ARG ALA GLN VAL MET ARG ALA PHE SER SER SER THR ASN LEU GLN GLU ARG PHE ARG ARG LYS ASP OP
CCT TGT GCC TGG GAG GTT GTC AGA GCA CAA GTC ATG AGA GCC TTC TCT TCC TCA ACA AAC TTG CAG GAG AGA TTC AGG AGA AAG GAC TGA
  800                                                               850

CACACACCTGGTTCAACACGGAAATGATTCTCACGGACCAACAGACCACACTTCCTCCTGCGCTGCCATGTGGAAGACTCATTTCTGCTGTCATCAGGCACTGAACTGAATCAATTTGTT
          900                                                     950                                                   1000

AAATGATTTCAGGTATATTATGTGACATCATGATCTACTCTACAGGCACTACTCTGTCCCAGATACTCAAGCTAATCCATCTACTTATTTATCTATTTGGTATTTATTTATCTAATTTAA
                                          1050                                                   1100

TATTTATTTATCTATATATAAAGAATTAAATTATTTTGTTCATATAATTATGTATGTATAATTAATGGAAAAATATATTTTGTATTTAGTCAATTTATGAGTTTTCTTCATTCATTAAAC
                    1150                                                   1200

CTTACTATAAAAATCTTCCTTTGTTTTTCTTTAAAAAAGAAACATGAAGACTGAATATGCAACTTGATTAAAGAATGCATTTTTATAATTCCTTCACCCATTTTTGTGATTTGCACATTA
1250                                                 1300                                                      1350

CAAATGGGGATTTTGGGGGGATTTTCTGACCGGAACTTGGAAGCGACGAACCTGAAAGAAGGACACTCAGACAGTCTCTTGCAAGGACTGACAAGTTTATTTC
                              1400                                                 1450
```

FIG. 3A-2

BoIFN-α2

```
GAAAAAAATATCTAAAAGGCTCTGTGGGCAGAAGAAAGAAGAGCAACATGAAAAAAAAAATGATTGGGTAGTGCAGCCC

TAACCCACTGGAGAGTGCAAACTGAAAAGCAAAAACAAAAGTAGAAAATAAGAGGGAACTTTCACAAAGTGGAAACCAT

GGGCTCCTATTTAAGACACAGGCCTGAAGGAAGGTCTTCAGAGAATCTAGAGAGCAGGTTCACAGAGTCACCCACTGCC

                                S1                                      S10
                                met ala pro ala trp ser phe leu leu ala leu leu
CCAGGGCAGAAGCATCTGCAAGGTCCCCG   ATG GCC CCA GCC TGG TCC TTC CTC CTG GCC CTG CTG

                            S20         S23  1
leu leu ser cys asn ala ile cys ser leu gly cys his leu pro his thr his ser leu
CTG CTC AGC TGC AAC GCC ATC TGC TCT TTG GGT TGC CAC CTG CCT CAC ACC CAC AGC CTG

10                                      20
pro asn arg arg val leu thr leu leu arg gln leu arg arg val ser pro ser ser cys
CCC AAC AGG AGG GTC CTG ACA CTC CTG CGA CAA CTG AGG AGG GTC TCC CCT TCC TCC TGC

30                                      40
leu gln asp arg asn asp phe ala phe pro gln glu ala leu gly gly ser gln leu gln
CTG CAG GAC AGA AAT GAC TTT GCA TTC CCC CAG GAG GCG CTG GGT GGC AGC CAG TTG CAG

50                                      60
lys ala gln ala ile ser val leu his glu val thr gln his thr phe gln leu phe ser
AAG GCT CAA GCC ATC TCT GTG CTC CAC GAG GTG ACC CAG CAC ACC TTC CAG CTC TTC AGC

70                                      80
thr glu gly ser ala ala val trp asp gln ser leu leu asp lys leu arg ala ala leu
ACA GAG GGC TCG GCC GCT GTG TGG GAC CAG AGC CTC CTG GAC AAG CTC CGA GCT GCA CTG
```

FIG. 3B-1

```
 90                                          100
asp gln gln leu thr asp leu gln ala cys leu arg gln glu glu gly leu arg gly ala
GAT CAG CAG CTC ACT GAC CTG CAA GCC TGT CTG AGG CAG GAG GAG GGG CTG CGA GGG GCT

110                                          120
pro leu leu lys glu asp ala ser leu ala val arg lys tyr phe his arg leu thr leu
CCC CTG CTC AAG GAG GAT GCC AGC CTG GCT GTG AGG AAA TAC TTC CAC AGA CTC ACT CTC

130                                          140
tyr leu gln glu lys arg his ser pro cys ala trp glu val val arg ala glu val met
TAT CTG CAA GAG AAG AGA CAC AGC CCT TGT GCC TGG GAG GTT GTC AGA GCA GAA GTC ATG

150                                          160                     166
arg ala phe ser ser ser thr asn leu gln glu lys phe arg arg lys asp OP
AGA GCC TTC TCT TCT TCA ACA AAC TTG CAG GAG AAA TTC AGG AGA AAG GAC TGA CACACA

CCTGGTTCAACACGGAAATGATTCTCATGGACCAACAGACCACACTTCCTCCTGCACTGCCATGTGGAAGACTCTCAT

TTCTGCTGTCATTGCACCCTGAAATGAATCAATATGTCAAATGATTTCTGGAATATTAAGTAACATCATGTTCTACTC

TATAGGCAAAACAGATGCCGAAGCTCATCTATCTACATATTTAACTACTTGGACATTTATTTATTTATTTTAATATTT

ATTTAACTATTTATAAATATTTAAATTATTTTGTTGATAAAGTATTATGTATGTACATTTAGGGGAAAATGTATATTT

TGTATTTAGTCAGTTTATGATTTTTCTTCCTTTATTAAATTTTTACTGTAAAAGACTTACTTTGTTTTTTCGTTAAAA

CAGAGCCACCAAGCCTGAATGGCAGCTTGATTAAAAATTGCATTTTATGATTCCTTGAGCCCTTTTTAGGATCTGCAT

GTTAGAAGTAAAAATACTCTAGCTCTAGCTATGTTTTTTGTTGCTCTGAGGACCTTGAAGGGAACATAACCACTCCAG

TGCTTTTTGTAACTCTGATTTTTTTTTCAAAAAAAAGTAACCTAAAAACAACCATCAAAAAAAAAATCCATGCTTCAG

GATTTGATGAATTC
```

FIG. 3B-2

BoIFN-α3

```
GGATCCACAGCATAAATGTGTTGTCACAATTTCACGGTGGGGGTAATTAGTAAAAAAAAAAATTTCAGAAGACTCTGTC

AATAGGGGAAGGGGGGTCAATAATGAAAACAACGTTTGCAAAATGCTGTCCTAAACCCATTTGGAGAGTGCAAAATGAA

AAACAAAAACAAAAGTAGAAAGCAAGAGGGAACTTTCAGAAAATGGAAACCATGGGCTCCTATTTAACACACAGGCCTG

AAGGAAGGTCTTCAGAGAACCTAGAAAGCAGGTTCACAGAGTCACCCACCTCCCCAGGCCACAAGCATCTGCAAGGTCC

    S1                                  S10
    met ala pro ala trp ser leu leu leu ala leu leu leu leu ser cys asn ala ile
CCA ATG GCC CCA GCC TGG TCC TTA CTG CTG GCC CTG CTG CTG CTC AGC TGC AAT GCC ATC

S20         S23  1                                   10
cys ser leu gly cys his leu pro his thr his ile leu ala asn arg arg val leu met
TGC TCT CTG GGC TGC CAC CTG CCT CAC ACC CAC ATC CTG GCC AAC AGG AGG GTC CTG ATG

            20                                      30
leu leu gly gln leu arg arg val ser pro ser ser cys leu gln asp arg asn asp phe
CTC CTG GGA CAA CTG AGG AGG GTC TCC CCT TCC TCC TGC CTG CAG GAC AGA AAT GAC TTT

            40                                      50
ala phe pro gln glu ala leu gly gly ser gln leu gln lys ala gln ala ile ser val
GCA TTC CCC CAG GAG GCG CTG GGT GGC AGC CAG TTG CAG AAG GCT CAA GCC ATC TCT GTG

            60                                      70
leu his glu val thr gln his thr phe gln leu phe ser thr glu gly ser ala thr met
CTC CAC GAG GTG ACC CAG CAC ACC TTC CAG CTT TTC AGC ACA GAG GGC TCG GCC ACC ATG
```

FIG. 3C-1

```
               80                                        90
trp asp glu ser leu leu asp lys leu arg asp ala leu asp gln gln leu thr asp leu
TGG GAT GAG AGC CTC CTG GAC AAG CTC CGC GAT GCA CTG GAT CAG CAG CTC ACT GAC CTG

               100                                       110
gln phe cys leu arg gln glu glu glu leu gln gly ala pro leu leu lys glu asp ser
CAA TTC TGT CTG AGG CAG GAG GAG GAG CTG CAA GGA GCT CCC CTG CTC AAG GAG GAC TCC

               120                                       130
ser leu ala val arg lys tyr phe his arg leu thr leu tyr leu gln glu lys arg his
AGC CTG GCT GTG AGG AAA TAC TTC CAC AGA CTC ACT CTC TAT CTG CAA GAG AAG AGA CAC

               140                                       150
ser pro cys ala trp glu val val arg ala gln val met arg ala phe ser ser ser thr
AGC CCT TGT GCC TGG GAG GTT GTC AGA GCA CAA GTC ATG AGA GCC TTC TCT TCC TCA ACA

               160                     166
asn leu gln glu ser phe arg arg lys asp OP
AAC TTG CAG GAG AGT TTC AGG AGA AAG GAC TGA CACACACCTGGTTCAACACGGAAATGATTCTCATGG

ACCAACAGACCACACTTCCTCCTGCGCTGCCATGTGGAAGATTCATTTCTGCTGTCATCAGGCACTGAACTGAATCAA

TTTGTTAAATGATTTCAGGTATATTAAGCGACATCATGATCTACTCTACAGGCACTACTCTGTCCCGGATACTCAAGC

TAATCCATCTACTTATTTATCTATTTGGATATTTATTTATCTAATTTAATATTTATTTATCTATATATAAAGAATTAA

ATTATTTTGTTCATATAATTATGTATGTATACTTAAGGGAAAAATATATTTTGTATTTAGTCAATTTATGAGTTTTCT

TCATTCATTAAACCTTACTATAAAAATCTTCCTTTGTTTTTCTTTAAAAAAGAAACATGAAGACTGAATACGCAACTT

GATTAAAGAATGCATTTTACAATTCCTTCACCCATGTTTGTGATTTCCACATTACAAGTGTTGGGGATTTTCTCCTCG

GGACTTGGAAGCGACGAACCTGAAAGAAGGACGGACAGTCTCTTGCAAGGACTGAC
```

FIG. 3C-2

BoIFN-α4

```
TCTAGAAGGAAAAGAAACATGGGAGGAGCTCATGGACTCACAATAATCAGCCTCTTCTCTAAATCAAACACTCAAGAAA

ACCCATCCTTTGTTTCAAACAGTTTCTTTGCTAGAGTGACCTGGTAAATGCCTGATAAACACAGAGCCTGCCTTCCTAA

GTAAAGTAAGAAACAGAAATAAGCCTAGGATCAGGGCCAAAAATGTGTTCATGAACAGAAAAGAGCCACATTTACACAT

GAAGAGAAAAGTGATATGTTTGTACTTAGAAACCTACATCATTTCTAATGTAAGACAAAGACCTTTCTCATTTGATTGA

TAAATATCCATTTGGATGGGTACATTTGAAGTTATTGGGAAATAGATAAAAGTAATAGTTTAGACTGATGACAATTTCT

TTGACCATATTCGGAATACATAAATGAAAATCAAAAAAGGAAGTACAAGTACACAGAAATGACTAGAAAATGAAAATTA

CTGTGTTCCCTATTTAATGGCCTTGCTTAGAAAGCATGGCATCAGAGAACCTACCTCAAGGTTCCACCAGACGCTGTCT

                                S1                                      S10
                                met ala phe val leu ser leu leu met ala leu val
CAGCCAGCCCAGCAGCAGCCTCATCTTCCCC ATG GCC TTC GTG CTC TCT CTA CTG ATG GCC CTG GTG

                            S20         S23  1
leu val ser tyr gly pro gly gly ser leu gly cys asp leu ser pro asn his val leu
CTG GTC AGC TAT GGC CCG GGA GGA TCC CTG GGC TGT GAC TTG TCT CCG AAC CAC GTG CTG

 10                                      20
val gly arg gln asn leu arg leu leu gly gln met arg arg leu ser pro arg phe cys
GTT GGC AGG CAG AAC CTC AGG CTC CTG GGC CAA ATG AGG AGA CTC TCC CCT CGC TTC TGT

 30                                      40
leu gln asp arg lys asp phe ala phe pro gln glu met val glu val ser gln phe gln
CTG CAG GAC AGA AAA GAC TTT GCT TTC CCC CAG GAG ATG GTG GAG GTC AGC CAG TTC CAG

 50                                      60
glu ala gln ala ile ser val leu his glu met leu gln gln ser phe asn leu phe his
GAG GCC CAG GCC ATT TCT GTG CTC CAT GAG ATG CTC CAG CAG AGC TTC AAC CTC TTC CAC
```

FIG. 3D-1

```
70                                      80
lys glu arg ser ser ala ala trp asp thr thr leu leu glu gln leu leu thr gly leu
AAA GAG CGC TCC TCT GCT GCC TGG GAC ACT ACC CTC CTG GAG CAG CTC CTC ACT GGA CTC

90                                      100
his gln gln leu asp asp leu asp ala cys leu gly leu leu thr gly glu glu asp ser
CAT CAG CAG CTG GAT GAC CTG GAT GCC TGT CTG GGC CTG TTG ACT GGA GAG GAA GAC TCT

110                                     120
ala leu gly arg thr gly pro thr leu ala met lys arg tyr phe gln gly ile his val
GCC CTG GGA AGG ACG GGC CCC ACA CTG GCC ATG AAG AGG TAC TTC CAG GGC ATC CAT GTC

130                                     140
tyr leu gln glu lys gly tyr ser asp cys ala trp glu ile val arg leu glu ile met
TAC CTG CAA GAG AAG GGA TAC AGC GAC TGT GCC TGG GAA ATC GTC AGA CTG GAA ATC ATG

150                                     160
arg ser leu ser ser ser thr ser leu gln glu arg leu arg met met asp gly asp leu
AGA TCC TTG TCT TCA TCA ACC AGC TTG CAA GAA AGG TTA AGA ATG ATG GAT GGA GAC CTG

170     172
lys ser pro OP
AAA TCA CCT TGA CATGACTCTCACTGACTAAGATGCCCCATCATCTTTGCACACTCATCTGTGGCCATTTCAAAA

GACTCTGATTTCTGTTGTAGCCACAAAATTTATTGAATTACTTCAGCCAATACTTTGTCAGTAGTAAATGAATATACA

TAAATTTTTTTGGCTGCAGGTGCATCAGTCCCGAAGTGAAGACTGCCCTTATTTTATTGTTTGCTTATTTATTTTGTT

ATATTTATTCTTTTATTTCCTCATATTTATTTTTCCATATAAAATATTTTTGTTTACATTGTATTAAAATTTAACAAA

TACATTAACATTTTTATTTCATTATATTTGTAATTTGTTTTATTTATTAAATATTGTCAAGGTGAACTTCTTGAATTT

TTTTACCGTTTTATGTTTAGTTGCCAGGTAAAGTCTGATTCTTTTGTGACCCCATAGACTGTAGCCCACCAGGCTCCT

CTGTCCATGGGATGATCAGGCAAGACTACTGGAGTATGTTGCCATTTACAGGGGATCTCCCAACCAAGGATGAAATC
```

FIG. 3D-2

```
                  S1                S10                 S20   S23                 10                  20                  30                  40
BoIFN-α1          M A P A W S L L L A L L L L S C N A I C S L G C H L P H S H S L A K R R V L T L L R Q L R R V S P S S C L Q D R N D F A F P Q
BoIFN-α2          M A P A W S F L L A L L L L S C N A I C S L G C H L P H T H S L P N R R V L T L L R Q L R R V S P S S C L Q D R N D F A F P Q
BoIFN-α3          M A P A W S L L L A L L L L S C N A I C S L G C H L P H T H I L A N R R V L M L L G Q L R R V S P S S C L Q D R N D F A F P Q
BoIFN-α4          M A F V L S L L M A L V L V S Y G P G G S L G C D L S P N H V L V G R Q N L R L L G Q M R R L S P R F C L Q D R K D F A F P Q
LeIF A            M A L T F A L L V A L L V L S C K S S C S V G C D L P Q T H S L G S R R T L M L L A Q M R K I S L F S C L K D R H D F G F P Q
LeIF B            M A L T F Y L M V A L V V L S Y K S F S S L G C D L P Q T H S L G N R R A L I L L A Q M R R I S P F S C L K D R H D F E F P Q
LeIF C            M A L S F S L L M A V L V L S Y K S I C S L G C D L P Q T H S L G N R R A L I L L G Q M G R I S P F S C L K D R H D F R I P Q
LeIF D            M A S P F A L L M V L V V L S C K S S C S L G C D L P E T H S L D N R R T L M L L A Q M S R I S P S S C L M D R H D F G F P Q
LeIF E                                                  L P L G C D L P Q A H S V G N R R A F I L L T Q M R R I S P F S Y L K D R H D F D F P H
LeIF F            M A L S F S L L M A V L V L S Y K S I C S L G C D L P Q T H S L G N R R A L I L L A Q M G R I S P F S C L K D R H D F G F P Q
LeIF G                                                                                                                            H D F G F P Q
LeIF H            M A L P F S L M M A L V V L S C K S S C S L G C N L S Q T H S L N N R R T L M L M A Q M R R I S P F S C L K D R H D F E F P Q
LeIF I            M A L S F S L L M A V L V L S Y K S I C S L G C D L P Q T H S L G N R R A L I L L A Q M G R I S P F S C L K D R P D F G L P Q
LeIF J            M A R S F S L L M V V L V L S Y K S I C S L G C D L P Q T H S L R N R R A L I L L A Q M G R I S P F S C L K D R H E F R F P E
LeIF K            M A L P F A L L M A L V V L S C K S S C S L D C D L P Q T H S L G H R R T M M L L A Q M R R I S L F S C L K D R H D F R F P Q

All Human         M A     F   L           V L S   K S     S     C   L     T H S L     R R       L     Q M     I S     S C L   D R     F     P
All Bovine        M A P A W S L L L A L L L L S C N A I C S L G C   L       H   L     R     L   L L   Q   R R   S P     C L Q D R   D   A F P Q
BoIFN-α1/Human    M A       S L L   A L L   L S C     I C S L G C     P     H S L     R R   L   L L   Q   R R   S P   S C L   D R   D F   F P Q
BoIFN-α4/Human                                            S L G C D L       H   L     R     L   L L   Q M R R   S P     C L   D R   D F   F P Q
```

FIG. 4A

```
                                  50                  60                  70                  80                  90                  100
BoIFN-α1        E A L G G S Q L Q K A Q A I S V L H E V T Q H T F Q L F S T E G S A A V W D E S L L D R L R T A L D Q Q L T D L Q A C L R Q E
BoIFN-α2        E A L G G S Q L Q K A Q A I S V L H E V T Q H T F Q L F S T E G S A A V W D Q S L L D K L R A A L D Q Q L T D L Q A C L R Q E
BoIFN-α3        E A L G G S Q L Q K A Q A I S V L H E V T Q H T F Q L F S T E G S A T M W D E S L L D K L R D A L D Q Q L T D L Q F C L R Q E
BoIFN-α4        E M V E V S Q F Q E A Q A I S V L H E M L Q Q S F N L F H K E R S S A A W D T T L L E Q L L T G L H Q Q L D D L D A C L G L L
LeIF A          E E F - G N Q F Q K A E T I P V L H E M I Q Q I F N L F S T K D S S A A W D E T L L D K F Y T E L Y Q Q L N D L E A C V I Q G
LeIF B          E E F D D K Q F Q K A Q A I S V L H E M I Q Q T F N L F S T K D S S A A L D E T L L D E F Y I E L D Q Q L N D L E V L C D Q E
LeIF C          E E F D G N Q F Q K A Q A I S V L H E M I Q Q T F N L F S T E D S S A A W E Q S L L E K F S T E L Y Q Q L N D L E A C V I Q E
LeIF D          E E F D G N Q F Q K A P A I S V L H E L I Q Q I F N L F T T K D S S A A W D E D L L D K F C T E L Y Q Q L N D L E A C V M Q E
LeIF E          Q V F H G N H F Q K V Q A I F L F H E M M Q Q T F N L F S T K D S S D T W D E T L L D K S Y T E L Y Q Q L N D L E A C V M * K
LeIF F          E E F D G N Q F Q K A Q A I S V L H E M I Q Q T F N L F S T K D S S A T W E Q S L L E K F S T E L N Q Q L N D M E A C V I Q E
LeIF G          E E F D G N Q F Q K A Q A I S V L H E M I Q Q T F N L F S T K D S S A T W D E T L L D K F Y T E L Y Q Q L N D L E A C M M Q E
LeIF H          E E F D G N Q F Q K A Q A I S V L H E M M Q Q T F N L F S T K N S S A A W D E T L L E K F Y I E L F Q Q M N D L E A C V I Q E
LeIF I          E E F D G N Q F Q K T Q A I S V L H E M I Q Q T F N L F S T E D S S A A W E Q S L L E K F S T E L Y Q Q L N N L E A C V I Q E
LeIF J          E E F D G H Q F Q K T Q A I S V L H E M I Q Q T F N L F S T E D S S A A W E Q S L L E K F S T E L Y Q Q L N D L E A C V I Q E
LeIF K          E E F D G N Q F Q K A E A I S V L H E V I Q Q T F N L F S T K D S S V A W D E R L L D K L Y T E L Y Q Q L N D L E A C V M Q E

All Human       E E F       Q F Q K       I   V L H E     Q Q   F N L F   T     S S             L L           E L   Q Q   N     E         Q
All Bovine      E         S Q   Q   A Q A I S V L H E     Q     F   L F     E   S         D     L L     L       L   Q Q L   D L   C L     Q
BoIFN-α1/Human  E       G   Q   Q K A Q A I S V L H E     Q   T F   L F S T     S   A   W D E S L L D       T   L   Q Q L   D L A C       Q E
BoIFN-α4/Human  E           Q F Q   A Q A I S V L H E M   Q Q   F N L F         S S A A W D   T L L E       T   L   Q Q L   D L A C
```

FIG. 4B

BoIFN-β1

```
AGTTTTAGAGGGCAACTAATAATTTAATGACATGGAAAAATGAAAGCGAGAACTGAAAGTGGGAAATTCCTCTGAAATA

GAAAGATGAGGGCCATGCTGTATAAGTAGCCCACACTAAGGACGAGGACATTCACTCTGCAAACCCTTGAAGACTCAGC

                                                S1
                                                met thr tyr arg cys leu leu gln
TTCAGCACCTACTAGCAGAACAGGTAGCCCTGTGCCTGATTTCATC  ATG ACC TAC CGG TGC CTC CTC CAG

    S10                                     S20     1
met val leu leu leu cys phe ser thr thr ala leu ser arg ser tyr ser leu leu arg
ATG GTT CTC CTG CTG TGT TTC TCC ACC ACA GCT CTT TCC AGG AGC TAC AGC TTG CTT CGA

        10                                      20
phe gln gln arg gln ser leu lys glu cys gln lys leu leu gly gln leu pro ser thr
TTC CAA CAA CGT CAG AGC CTT AAA GAG TGT CAG AAA CTC CTG GGG CAG TTA CCT TCA ACT

        30                                      40
ser gln his cys leu glu ala arg met asp phe gln met pro glu glu met lys gln glu
TCT CAA CAT TGC CTC GAG GCC AGG ATG GAC TTC CAG ATG CCT GAG GAG ATG AAG CAA GAA

        50                                      60
gln gln phe gln lys glu asp ala ile leu val met tyr glu val leu gln his ile phe
CAG CAG TTC CAG AAG GAA GAT GCC ATA TTG GTC ATG TAT GAG GTG CTC CAG CAC ATC TTC

        70                                      80
gly ile leu thr arg asp phe ser ser thr gly trp ser glu thr ile ile glu asp leu
GGC ATT CTC ACC AGA GAC TTC TCC AGC ACT GGC TGG TCT GAG ACC ATC ATC GAG GAC CTC
```

FIG. 9A-1

```
        90                                                100
leu lys glu leu tyr trp gln met asn arg leu gln pro ile gln lys glu ile met gln
CTT AAG GAA CTC TAT TGG CAG ATG AAT CGT CTG CAG CCA ATC CAG AAG GAA ATA ATG CAG

        110                                               120
lys gln asn ser thr thr glu asp thr ile val pro his leu gly lys tyr tyr phe asn
AAG CAA AAC TCC ACT ACG GAA GAC ACG ATC GTT CCC CAC CTA GGG AAA TAT TAC TTC AAC

        130                                               140
leu met gln tyr leu glu ser lys glu tyr asp arg cys ala trp thr val val gln val
CTC ATG CAG TAC CTG GAG TCC AAG GAG TAC GAC AGG TGT GCC TGG ACA GTC GTG CAA GTG

        150                                               160                 165
gln ile leu thr asn val ser phe leu met arg leu thr gly tyr val arg asp OP
CAA ATA CTC ACG AAC GTT TCT TTC CTG ATG AGA CTA ACA GGT TAC GTC CGT GAC TGA ACA

TCTCCCACCTGTGGCTCTGGGAAGGGACAATGTGACTTTGAGGTGAGACTCTTCACCCAGCAGAGGCTCTTGAAGTAA

CTGACAATGCAATGCACTGGATTTCAATGGACAGTTAAGACTAAGCTATTTTAAATTGATTTATGCATTATTTATTTA

TTTATTTAATGAGAAATAAATTATTTATCAAAATTTATTTAATGAGAAATAAATTATTTATGAAACAAAAGTCAACGT

GGCAGTTTCAATCTCAACTTGATTTATGTGACAACACATATTAAAAATTGCAGAGCACTTTGGAGACATTCATTGCAA

AACAAGCCTGCAGAGTAGTAGAGTTTCTGGCCCTGCCTTTGAGGCATTTAAAATACAAGGAAGCTGTTTGGAATGTCC

AAGTTATATGCATGCTCTCCATGT
```

FIG. 9A-2

```
BoIFN-β2

TTTTAGCATTTAGCAATTCACTGAAAATTTACAAAAACATTAGAAATTCTCCCAGACTGTATATCTTTTTCCCCTTAAT

ACATATAAAATCAAAAAGCAAGGAGCTAAAAAGAAAAAGAGTTTTAGAGGTAACTAATCAACACAGGAGAACTAAAAAG

GAAACTGGAAAGTGGGAAATTCCTCTCCAATAGAAAGAATGGAGGGCCATGCTGTATAAGTAGCCCACACTCAAGAAGG

AAGGCCATTCACTCTGCAAACCCTTGAAGACTCAGCTTCAGCACCTACTAGCAGAACAGGCAGCCCTGTGCCTGATTTC

    S1                                    S10
    met thr his arg cys leu leu gln met val leu leu leu cys phe ser thr thr ala
ATC ATG ACC CAC CGG TGC CTC CTC CAG ATG GTT CTC CTG CTG TGT TTC TCC ACC ACA GCT

S20     1                                     10
leu ser arg ser tyr ser leu leu arg phe gln gln arg arg ser leu glu leu cys gln
CTT TCC AGG AGC TAC AGC TTG CTT CGA TTC CAA CAA AGG CGG AGC CTT GAG TTA TGT CAG

    20                                        30
lys leu leu arg gln leu pro ser thr pro gln his cys leu glu ala lys met asp phe
AAA CTC CTG AGG CAG TTA CCT TCA ACT CCT CAA CAT TGC CTC GAG GCC AAG ATG GAC TTC

    40                                        50
arg met pro glu glu met lys gln ala gln gln phe arg lys glu asp ala ile leu val
CGG ATG CCT GAG GAG ATG AAG CAA GCA CAG CAG TTC CGG AAG GAA GAT GCC ATA TTG GTC

    60                                        70
ile tyr glu met leu gln gln ile phe asn ile leu thr arg asp phe ser ser thr gly
ATC TAT GAG ATG CTC CAG CAG ATC TTC AAT ATT CTC ACC AGA GAC TTC TCC AGC ACT GGC
```

FIG. 9B-1

```
 80                                                                 90
trp ser glu thr ile ile glu asp leu leu glu glu leu tyr glu gln met asn his leu
TGG TCT GAG ACC ATC ATC GAG GAC CTC CTT GAG GAA CTC TAT GAG CAG ATG AAT CAT CTG

 100                                                                110
glu pro ile gln lys glu ile met gln lys gln asn ser thr met gly asp thr thr val
GAG CCA ATC CAG AAG GAA ATA ATG CAG AAG CAA AAC TCC ACT ATG GGA GAC ACA ACC GTT

 120                                                                130
leu his leu arg lys tyr tyr phe asn leu val gln tyr leu lys ser lys glu tyr asn
CTT CAC CTG AGG AAA TAT TAC TTC AAC CTC GTG CAG TAC CTA AAG TCC AAG GAG TAC AAC

 140                                                                150
arg cys ala trp thr val val arg val gln ile leu arg asn phe ser phe leu thr arg
AGG TGT GCC TGG ACA GTC GTG CGA GTG CAA ATA CTC AGG AAT TTT TCT TTC CTG ACG AGA

 160                     165
leu thr gly tyr leu arg glu OP
CTA ACA GGT TAC CTC CGT GAA TGA ACATCTCCCACCTGTGGCTCTGGGATTGACAATGTGACTTTGAGGTGA

GACTCTTCACCCAGTAGAGGCTCTTGAAGTAACTGACAATGCAATGCAATGGACAGTTAAATACTGTAAGCTATTTTT

AAATTGATTTATGCATTATTTATTTATTTAAACTTTTATATGGGAAATAAATTATTTATGAAACAAAATTGAACATGG

CAGTTTTAATGTCAACTTGATTGATGTGACAACATATATTAAAAATTGGCGAGCACCCTGGAGACATTTATTGCAAAA
```

FIG. 9B-2

BoIFN-β3

```
TTGCATAAGAGGCTATTTAGTCCTCTTCTACTTTCTGCCAAAGTTATAGAGGCAACGAATAATTTAAATGACAAAGGAA

AACTGAAAGGGAGAACTGAAAGTGGGAAATCTCTCCGAGGGCCATCCTATATAAGTAGCCCACACTCAAGGAGGAAGGC
CATTCACTCTGCAAGCCCTTGAAGACTCAGCGTCAGCATCTACTAGCAGAACGGGCAGCCCTGTGCCTGTTTTCATC

 S1                                  S10                                     S20
met thr tyr arg cys leu leu pro met val leu leu leu cys phe ser thr thr ala leu
ATG ACC TAC CGG TGC CTC CTC CCG ATG GTT CTC CTG CTG TGT TTC TCC ACC ACA GCT CTT

      1                                     10
ser arg ser tyr ser leu leu arg phe gln gln arg arg ser ala glu val cys gln lys
TCC AGG AGC TAC AGC TTG CTC AGA TTC CAG CAA AGG CGG AGC GCT GAG GTG TGT CAG AAA

 20                                     30
leu leu gly gln leu his ser thr pro gln his cys leu glu ala lys met asp phe gln
CTC CTG GGG CAG TTA CAT TCA ACG CCT CAA CAT TGC CTC GAG GCC AAG ATG GAC TTC CAA

 40                                     50
val pro glu glu met asn gln ala gln gln phe arg lys glu asp ala ile leu val ile
GTC CCT GAG GAG ATG AAC CAA GCA CAG CAG TTC CGG AAG GAA GAT GCC ATA TTG GTC ATC

 60                                     70
tyr glu met leu gln gln ile phe asn ile leu thr arg asp phe ser ser thr gly trp
TAT GAG ATG CTC CAG CAG ATC TTC AAT ATT CTC ACC AGA GAC TTC TCC AGC ACT GGC TGG
```

FIG. 9C-1

```
80                                      90
ser glu thr ile ile glu asp leu leu val glu leu tyr gly gln met asn arg leu gln
TCT GAG ACC ATC ATT GAG GAC CTC CTT GTG GAA CTC TAT GGG CAG ATG AAT CGT CTG CAG

100                                     110
pro ile gln lys glu ile met gln glu gln asn phe thr met gly asp thr thr val leu
CCA ATC CAG AAG GAA ATA ATG CAG GAG CAA AAC TTC ACC ATG GGG GAC ACA ACC GTT CTT

120                                     130
his leu lys lys tyr tyr phe asn leu val gln tyr leu glu ser lys glu tyr asn arg
CAC CTG AAG AAG TAT TAC TTC AAC CTC GTG CAG TAC CTG GAG TCC AAG GAG TAC AAC AGG

140                                     150
cys ala trp thr val val arg val gln ile leu thr asn phe ser phe leu met arg leu
TGT GCC TGG ACA GTC GTG CGA GTG CAA ATA CTC ACG AAC TTT TCT TTC CTG ATG AGA CTA

160                 165
thr ala ser leu arg asp OP
ACA GCT TCC CTC CGT GAC TGA ACACCTCCCACCTGTGGCTCTGGGAAGGGACAATGTGACTTTGAGCTGAGA

TGCTTCAGCCAGCAGAGGCTCTTAAAGTAACTGACAGTGCAATGCACGATTTCAATGAACAATAAAGACTAAGCTATT

TTTAAATTGATTTATGCGTTATTTCATTCATTTAAACTTTTATGTGAGAAATAAAT
```

FIG. 9C-2

```
            S1                 S10                     S20  1                     10                      20                       30                      40
            .                  .                       .    .                     .                       .                        .                       .
BoIFN-β1    M T Y R C L L Q M V L L L C F S T T A L S R S Y S L L R F Q Q R Q S L K E C Q K L L G Q L P S T S Q H C L E A R M D F Q M P E
BoIFN-β2    M T H R C L L Q M V L L L C F S T T A L S R S Y S L L R F Q Q R R S L E L C Q K L L R Q L P S T P Q H C L E A K M D F R M P E
BoIFN-β3    M T Y R C L L P M V L L L C F S T T A L S R S Y S L L R F Q Q R R S A E V C Q K L L G Q L H S T P Q H C L E A K M D F Q V P E
HuIFN-β     M T N K C L L Q I A L L L C F S T T A L S M S Y N L L G F L Q R S S N F Q C Q K L L W Q L N G R L E Y C L K D R M N F D I P E

                           50                      60                      70                      80                      90                      100
                           .                       .                       .                       .                       .                       .
BoIFN-β1    E M K Q E Q Q F Q K E D A I L V M Y E V L Q H I F G I L T R D F S S T G W S E T I I E D L L K E L Y W Q M N R L Q P I Q K E I
BoIFN-β2    E M K Q A Q Q F R K E D A I L V I Y E M L Q Q I F N I L T R D F S S T G W S E T I I E D L L E E L Y E Q M N H L E P I Q K E I
BoIFN-β3    E M N Q A Q Q F R K E D A I L V I Y E M L Q Q I F N I L T R D F S S T G W S E T I I E D L L V E L Y G Q M N R L Q P I Q K E I
HuIFN-β     E I K Q L Q Q F Q K E D A A L T I Y E M L Q N I F A I F R Q D S S S T G W N E T I V E N L L A N V Y H Q I N H L K T V L E E K

                   110                     120                     130                     140                     150                     160
                   .                       .                       .                       .                       .                       .
BoIFN-β1    M Q K Q N S T T E D T I V - P H L G K Y Y F N L M Q Y L E S K E Y D R C A W T V V Q V Q I L T N V S F L M R L T G Y V R D
BoIFN-β2    M Q K Q N S T M G D T T V - L H L R K Y Y F N L V Q Y L K S K E Y N R C A W T V V R V Q I L R N F S F L T R L T G Y L R E
BoIFN-β3    M Q E Q N F T M G D T T V - L H L K K Y Y F N L V Q Y L E S K E Y N R C A W T V V R V Q I L T N F S F L M R L T A S L R D
HuIFN-β     L E K E D F T R G K L M S S L H L K R Y Y G R I L H Y L K A K E Y S H C A W T I V R V E I L R N F Y F I N R L T G Y L R N
```

FIG. 10

```
             S1                S10                 S20 1                10                  20                  30
HuIFN-γ      M K Y T S Y I L A F Q L C I V L G S L G C Y C Q D P Y V K E A E N L K K Y F N A G H S D V A D N G T L F L G I
MuIFN-γ      M N A T H C I L A L Q L F L M A V S G - C Y C H G T V I E S L E S L N N Y F N S S G I D V E E K - S L F L D I
BoIFN-γ      M K Y T S Y F L A L L L C G L L G F S G S Y G Q G Q F F R E I E N L K E Y F N A S S P D V A K G G P L F S D I
consensus    M - - T - - - L A - - - - - - - - - - - - Y - - - - - - - - - E - L - - Y F N - - - - D V - - - - - L F - - I

                     40                  50                  60                  70                  80                  90
HuIFN-γ      L K N W K E E S D R K I M Q S Q I V S F Y F K L F K N F K D D Q S I Q K S V E T I K E D M N V K F F N S N K K
MuIFN-γ      W R N W Q K D G D M K I L Q S Q I I S F Y L R L F E V L K D N Q A I S N N I S V I E S H L I T T F F S N S K A
BoIFN-γ      L K N W K D E S D K K I I Q S Q I V S F Y F K L F E N L K D N Q V I Q R S M D I I K Q D M F Q K F L N G S S E
consensus    - - N W - - - - D - K I - Q S Q I - S F Y - - L F - - - K D - Q - I - - - - - - I - - - - - - - F - - - - - -

                               100                 110                 120                 130                 140          146
HuIFN-γ      K R D D F E K L T N Y S V T D L N V Q R K A I H E L I Q V M A E L S P A A K T G K R K R S Q M L F R - G R R A S Q
MuIFN-γ      K K D A F M S I A K F E V N N P Q V Q R Q A F N E L I R V V H Q L L P E S S L R K R K R S R C W F G V G K R L S Q
BoIFN-γ      K L E D F K K L I Q I P V D D L Q I Q R K A I N E L I K V M N D L S P K S N L R K R K R S Q N L F R - G R R A S M
consensus    K - - - F - - - - - - - V - - - - - Q R - A - - E L I - V - - - L - P - - - - - K R K R S - - - F - - G - R - S -
```

FIG. 13

```
  1 GAATTCATTC CTATTAAGAC ACAGGCCTCG AGGGAAGGTC TTCAGACATC CTAGAGAGCA GGGTCACAGA GTCACCCACC TCAGCCAGGA CAGAAGCATC

101 TGCAAGGTTC CCA  ATG GCC CCA ACC TCA GCC TTC CTC ACG GCC CTG GTG CTA CTC AGC TGC AAT GCC ATC TGC TCT CTG GGC
-23                 Met Ala Pro Thr Ser Ala Phe Leu Thr Ala Leu Val Leu Leu Ser Cys Asn Ala Ile Cys Ser Leu Gly

183 TGT GAC CTG CCT CAG ACC CAC AGC CTG GCT CAC ACC AGG GCC CTG AGG CTC CTG GCA CAA ATG AGG AGA ATC TCT CCC TTC
  1 Cys Asp Leu Pro Gln Thr His Ser Leu Ala His Thr Arg Ala Leu Arg Leu Leu Ala Gln Met Arg Arg Ile Ser Pro Phe

264 TCC TGC CTG GAC CAC AGA AGG GAC CTT GGA TCC CCT CAT GAG GCT TTT GGG GGC AAC CAG GTC CAG AAG GCT CAA GCC ATG
 28 Ser Cys Leu Asp His Arg Arg Asp Leu Gly Ser Pro His Glu Ala Phe Gly Gly Asn Gln Val Gln Lys Ala Gln Ala Met

345 GCT CTG GTG CAT GAG ATG CTC CAG CAG ACC TTC CAG CTC TTC AGC ACA GAG GGC TCG GCT GCT GCC TGG AAT GAG AGC CTC
 55 Ala Leu Val His Glu Met Leu Gln Gln Thr Phe Gln Leu Phe Ser Thr Glu Gly Ser Ala Ala Ala Trp Asn Glu Ser Leu

426 CTG CAC CAG TTC TGC ACT GGA CTG GAT CAG CAG CAC AGG GAC CTG GAA GCC TGT GTC ATG CAG GAG GCG GGG CTG GAA GGG
 82 Leu His Gln Phe Cys Thr Gly Leu Asp Gln Gln His Arg Asp Leu Glu Ala Cys Val Met Gln Glu Ala Gly Leu Glu Gly

507 ACC CCC CTG CTG GAG GAG GAC TCC ATC CTG GCT GTG AGG AAA TAC TTC CAC AGA CTC ACC CTC TAT CTG CAA GAG AAG AGC
109 Thr Pro Leu Leu Glu Glu Asp Ser Ile Leu Ala Val Arg Lys Tyr Phe His.Arg Leu Thr Leu Tyr Leu Gln Glu Lys Ser

588 TAC AGC CCC TGT GCC TGG GAG ATC GTC AGG GCA GAA GTC ATG AGA TCC TTC TCT TCC TCC AGA AAC CTG CAA GAC AGA CTC
136 Tyr Ser Pro Cys Ala Trp Glu Ile Val Arg Ala Glu Val Met Arg Ser Phe Ser Ser Ser Arg Asn Leu Gln Asp Arg Leu

669 AGG AAG AAG GAG TGA  CAGACAC TGGTTCATCA TAGAATGCTT CTTACAG
163 Arg Lys Lys Glu OP*
```

FIG. 14A

```
  1 ATGAATGCTA ACAAACTCAA ATGACATAGG AAAACTGAAA GGGAGAACTG AAAGTGGGAA ATTCCTCTGA ACTAGAAAGA GTGGAGGGCC TTCCAGTATA

101 AATAGCCTAT GGAGAAAGAA CATTCACACT GCACACTCCT GAAGACTTCA CTTCAGCACT TGAGTAGTGG AGCCAGTAAC CGTGTTTCCG TTTTCATCA

200 ATG GCT AAC AAG TGC ATC CTC CAA ATC GCT CTC CTG ATG TGT TTC TCC ACC ACA GCT CTT TCC ATG AGC TAT GAT GTG CTT
-23 Met Ala Asn Lys Cys Ile Leu Gln Ile Ala Leu Leu Met Cys Phe Ser Thr Thr Ala Leu Ser Met Ser Tyr Asp Val Leu

281 CGA TAC CAA CAA AGG AGC AGC AAT TTG GCA TGT CAG AAG CTC CTG GGA CAG TTG CCT GGG ACT CCT CAA TAT TGC CTC GAA
  5 Arg Tyr Gln Gln Arg Ser Ser Asn Leu Ala Cys Gln Lys Leu Leu Gly Gln Leu Pro Gly Thr Pro Gln Tyr Cys Leu Glu

362 GAT AGG ATG AAC TTT GAG GTC CCT GAG GAG ATT ATG CAA CCA CCA CAA TTC CAG AAG GAA GAT GCA GTA TTG ATT ATC CAC
 32 Asp Arg Met Asn Phe Glu Val Pro Glu Glu Ile Met Gln Pro Pro Gln Phe Gln Lys Glu Asp Ala Val Leu Ile Ile His

443 GAG ATG CTC CAG CAG ATC TTC GGC ATT CTC AGA AGA AAT TTC TCT AGC ACT GGC TGG AAT GAA ACC GTC ATT AAG ACT ATC
 59 Glu Met Leu Gln Gln Ile Phe Gly Ile Leu Arg Arg Asn Phe Ser Ser Thr Gly Trp Asn Glu Thr Val Ile Lys Thr Ile

524 CTT GTG GAA CTT GAT GGG CAG ATG GAT GAC CTG GAG ACA AGT CGC GTG GAG GAA ATC ATG GAG GAG GAA AAT TTC CCC AGG
 86 Leu Val Glu Leu Asp Gly Gln Met Asp Asp Leu Glu Thr Ser Arg Val Glu Glu Ile Met Glu Glu Glu Asn Phe Pro Arg

605 GGA GAC ATG ACC ATT CTT CAC CTG AAG AAA TAT TAC TTG AGC ATT CTG CAG TAC CTG AAG TCC AAG GAG TAC AGA AGC TGT
113 Gly Asp Met Thr Ile Leu His Leu Lys Lys Tyr Tyr Leu Ser Ile Leu Gln Tyr Leu Lys Ser Lys Glu Tyr Arg Ser Cys

686 GCC TGG ACA GTC GTC CAA GTG GAA ATC CTC AGG AAC TTT TCT TTC CTT AAC AGA CTT ACA GAT TAC CTC CGG AAC TGA  ACAT
140 Ala Trp Thr Val Val Gln Val Glu Ile Leu Arg Asn Phe Ser Phe Leu Asn Arg Leu Thr Asp Tyr Leu Arg Asn OP*

768 CTC CCCCCTGTGG CTCTGGGAAT TGACCATGTT GGCAATGATG TCAGGCTCTT CAAGCAGGGG AAGCTCTTTC AGTGACTGAC AGACAATGCA CTGAAT

867 TTGA ATGGACTGTT AAAGACTTTT AGCTTTTTTA ATAATAATTT ATGCATTAAA TTATGTATTT AATTTTTTAC CTTGGTGGAT TTTCTGTGTG AATCG

966 GCGGG TTACGAACCT GACTTGTATC CATGAGGATG TGAGTTTGAT CGAGGCCTCG ATCAGTGGGT TAAGGATCC
```

FIG. 14B

```
  1 GCATCGATCA GCTATTGCAG AAGAAAGGTC AGCCAAGCGC TCTGGGCCGT ATCGACTGTA TATAGGAGCT TCTGATTTCA ACCGAGAAGC TAACTCTCTC

101 CGAAACA ATG AGT TAT ACA ACT TAT TTC TTA GCT TTT CAA CTT TGC GTG ACT TTG TGT TTT TCT GGC TCT TAC TGC CAG GCG
            Met Ser Tyr Thr Thr Tyr Phe Leu Ala Phe Gln Leu Cys Val Thr Leu Cys Phe Ser Gly Ser Tyr Cys Gln Ala
                        -20                                     -10

183 CCC TTT TTT AAA GAA ATA ACG ATC CTA AAG GAC TAT TTT AAT CGA AGT ACC TCA GAT GTA CCT AAT GGT GGA CCT CTT TTC
    Pro Phe Phe Lys Glu Ile Thr Ile Leu Lys Asp Tyr Phe Asn Arg Ser Thr Ser Asp Val Pro Asn Gly Gly Pro Leu Phe
                                10                                      20

264 TTA GAA ATT TTG AAG AAT TGG AAA GAG GAG AGT GAC AAA AAA ATA ATT CAG AGC CAA ATT GTC TCC TTC TAC TTC AAA TTC
    Leu Glu Ile Leu Lys Asn Trp Lys Glu Glu Ser Asp Lys Lys Ile Ile Gln Ser Gln Ile Val Ser Phe Tyr Phe Lys Phe
    30                                      40                                      50

345 TTT GAA ATC TTC AAA GAT AAC CAG GCC ATT CAA AGG AGC ATG GAT GTG ATC AAG CAA GAC ATG TTT CAG AGG TTC CTA AAT
    Phe Glu Ile Phe Lys Asp Asn Gln Ala Ile Gln Arg Ser Met Asp Val Ile Lys Gln Asp Met Phe Gln Arg Phe Leu Asn
                60                                      70                                  80

426 GGT AGC TCT GGG AAA CTG AAT GAC TTC GAA AAG CTG ATT AAA ATT CCG GTA GAT AAT CTG CAG ATC CAG CGC AAA GCC ATC
    Gly Ser Ser Gly Lys Leu Asn Asp Phe Glu Lys Leu Ile Lys Ile Pro Val Asp Asn Leu Gln Ile Gln Arg Lys Ala Ile
                            90                                      100                                     110

507 AGT GAA CTC ATC AAA GTG ATG AAT GAT CTG TCA CCA AGA TCT AAC CTA AGA AAG CGG AAG AGA AGT CAG ACT ATG TTC CAA
    Ser Glu Leu Ile Lys Val Met Asn Asp Leu Ser Pro Arg Ser Asn Leu Arg Lys Arg Lys Arg Ser Gln Thr Met Phe Gln
                                        120                                     130

588 GGC CAG AGA GCA TCA AAA TAA  TT GTCATCCTGC CTGCAATATT TGAATTTTTA AATCTCAATC TATTTATTAA TATTTAATAT TTTACATTAT T
    Gly Gln Arg Ala Ser Lys OC*
            140

682 TATATGGGG AATATTGATT CATTGATCAA AGTATTTATA ATCTAACTTT TATGTGATGA AAATGGGTAT CTATTAACAT ATGTGTTATT TATGATTCCT G

782 TATCCTGTG ACTATTTCAC TTGACCTCTA TTTTCTCTGA TTAACTAGGC AATCTAGTTT TC
```

FIG. 14C

```
  1 AGAGACTGCT ATTAACTTAA ATGACATAGG AAAACTGAAA GGGAGAACTG AAAGTGGAAA TTCCTATGAA ATAGAAAGGG GACCATCCTG TATAAATAGG

101 CCATAGTCAT GGAAGAAGGG CATTCACACT GCAAACTCTC GAAGTCTTTC TTCAGCACCT AGACAGTAGC AGGCAAGACT TCCTAATTTC ATC  ATG
-23                                                                                                        Met

197 ACC GGC AGG TGC ATC CTC CAA ATC GCT CTC TTG GTG TGT TTC TTC ACC ACC GCG CAT TCC GTG AGC TAC AAG TTG CTT GGA
-22 Thr Gly Arg Cys Ile Leu Gln Ile Ala Leu Leu Val Cys Phe Phe Thr Thr Ala His Ser Val Ser Tyr Lys Leu Leu Gly

278 TTC CAA CTA AGA AGC AGC AGT TTG GAG TGT CAG GAG CTC CTG GTG AAC TTG AAC AGA ACC TCT AAA TAT TGC CTC AAG GAC
  6 Phe Gln Leu Arg Ser Ser Ser Leu Glu Cys Gln Glu Leu Leu Val Asn Leu Asn Arg Thr Ser Lys Tyr Cys Leu Lys Asp

359 AGG ATG AAC TTC GAG GTC CCT GAG GAG ATT AAA AAA TCA CAG CGG TTC CAG AAG GAG GAA GCC ATA TTG GTC ATC AAC GAG
 33 Arg Met Asn Phe Glu Val Pro Glu Glu Ile Lys Lys Ser Gln Arg Phe Gln Lys Glu Glu Ala Ile Leu Val Ile Asn Glu

440 ATG TTC CAG AAG ATC TTT AAT ATT TTC AGT AGA AGC ACC TCT AGC ACG GGA TGG AAT GAG ACC ACT GTT GAG AAC CTC CTT
 60 Met Phe Gln Lys Ile Phe Asn Ile Phe Ser Arg Ser Thr Ser Ser Thr Gly Trp Asn Glu Thr Thr Val Glu Asn Leu Leu

521 GCG ACA CTC CAC TGG CAG AAG GAA CAC CTG GAA ACG ATC CTG GAG GAA ATC ATG GAG GAG GAA AAC TTC ACC TGG GAC AAT
 87 Ala Thr Leu His Trp Gln Lys Glu His Leu Glu Thr Ile Leu Glu Glu Ile Met Glu Glu Glu Asn Phe Thr Trp Asp Asn

602 ACG ACC CTT CTG AAC CTG AAG AAA TAC TAC TTA AGG ATT GTG CGG TAC CTG AAG GCC AAG GAG TAC AGC GTC TGT GCC TGG
114 Thr Thr Leu Leu Asn Leu Lys Lys Tyr Tyr Leu Arg Ile Val Arg Tyr Leu Lys Ala Lys Glu Tyr Ser Val Cys Ala Trp

683 ACA GTA GTC CAC GCA GAA ATC CTC AGA AAC TTT TTC TTC CTT GAG AGA CTT ACA GAT TAT CAC CAA AAC TGA  AGCTCT CCCAG
141 Thr Val Val His Ala Glu Ile Leu Arg Asn Phe Phe Phe Leu Glu Arg Leu Thr Asp Tyr His Gln Asn OP*

766 CCTAT GCGCCTGGCC CTGAGAGAGT TGCAGCCAAG CGGTCCACGT GGTTTGCCCC AGCAGGCGAA AATCCTGTTT GATGGTGGTT CCGAAATCGG CAAA

865 ATCCCT TATAAATCAA AG
```

FIG. 14D

```
   1 TCTAGAGTCG AGACGCCAAC TTCTTCAGCC TCACTCTCTC CGAAGCA ATG AGT TAT ACA AGT TAC ATC TTG GCT TTT CAG CTC TGC CTC
                                                        Met Ser Tyr Thr Ser Tyr Ile Leu Ala Phe Gln Leu Cys Leu
                                                                    -20                                     -10

  90 ATC TTG GGT TCT TAC GGC TGT TAC TGC CAG GAC ACA CTA ACC AGA GAA ACA GAA CAC CTA AAG GCA TAT TTG AAA GCA AAT
     Ile Leu Gly Ser Tyr Gly Cys Tyr Cys Gln Asp Thr Leu Thr Arg Glu Thr Glu His Leu Lys Ala Tyr Leu Lys Ala Asn
                                                                             10

 171 ACA TCA GAT GTG GCA AAT GGT GGA CCC CTT TTC TTG AAT ATT TTG AGG AAT TGG AAA GAG GAG AGT GAC AAC AAA ATA ATT
     Thr Ser Asp Val Ala Asn Gly Gly Pro Leu Phe Leu Asn Ile Leu Arg Asn Trp Lys Glu Glu Ser Asp Asn Lys Ile Ile
          20                                     30                                  40

 252 CAG AGC CAA ATT GTC TCC TTC TAC TTC AAA CTC TTT GAC AAC TTA AAA GAC CAT GAG GTC ATC AAG AAG AGT ATG GAA TCC
     Gln Ser Gln Ile Val Ser Phe Tyr Phe Lys Leu Phe Asp Asn Leu Lys Asp His Glu Val Ile Lys Lys Ser Met Glu Ser
                      50                                     60                                  70

 333 ATC AAA GAA GAC ATA TTT GTG AAG TTC TTC AAT AGC AAC CTC ACT AAG ATG GAT GAC TTC CAA AAT CTG ACT CGA ATT TCG
     Ile Lys Glu Asp Ile Phe Val Lys Phe Phe Asn Ser Asn Leu Thr Lys Met Asp Asp Phe Gln Asn Leu Thr Arg Ile Ser
                                  80                                     90

 414 GTG GAT GAT CGG CTG GTC CAG CGT AAA GCA GTA AGT GAA CTC TCC AAT GTG CTG AAT TTT CTG TCT CCA AAA TCC AAC CTA
     Val Asp Asp Arg Leu Val Gln Arg Lys Ala Val Ser Glu Leu Ser Asn Val Leu Asn Phe Leu Ser Pro Lys Ser Asn Leu
     100                                     110                                     120

 495 AAG AAG CGA AAA AGG AGT CAG ACG CTG TTT CGA GGT CGG CGA GCA TCC AAG TAC TGA  TCAACTCAC CTGCAATATT TGAATTTTTA T
     Lys Lys Arg Lys Arg Ser Gln Thr Leu Phe Arg Gly Arg Arg Ala Ser Lys Tyr OP*
                 130                                     140

 582 CTAAATCTA TTTATTAATA TTTAACATTA TTTATATGGA AATCTACTTT TGATGCATCA ATTAAAAAGT ATTTATAATG GCAACTTTTA TGTAATGAAA A

 682 TGATTATCT ATTTATGTAT GTTATTTATA ATTCCTGAAT CATGTAACTA TTTCACTTGA CTCTTTTTTT CTCTGACTAA TTAGGCAATA CTATGTGATT A

 782 TAAGGCTTT ATACCTGGGG CCAAATAGGC AACTATTCTA AGCAAGATCC TATGCACTGT GCATTTATTT CACTTGAATG AATACTTGTG CACAAAATTA T

 882 ACAATCTAG TTGCTGCCTG TACTGTCCAG TTGCTGCCTA TTTGAGAACA TGTCTGCATT CTGAGCCACT GCTTTAATGG CAGTCAAACA GCACTTGAAC A

 982 TGTCAGGTG ATGTGACCTT GTCCTCTGAT AAAAACAGCA TCTCAGGAGA TTTCATGCCT GGTACTTCTG AATATTGTTG ACAACTGTGA CTGCCCCTGA A

1082 TGGAAAGTA ATTCACTTGT TCAGTTTATC AATGTCTAAT ATATATGAAT AAAGTATAAT TTTACAACTA AAAAAAAAAA AAAAA
```

FIG. 14E

Gamma Interferon Homologies

```
Human      -23 MKYTSYILAFQLCIVLGSLGCYCQDPYVKEAENLKKYFNAGHSDVADNGTLFLGILKNWK
Bovine     -23 MKYTSYFLALLLCGLLGFSGSYGQGQFFREIENLKEYFNASSPDVAKGGPLFSEILKNWK
Porcine    -23 MSYTTYFLAFQLCVTLCFSGSYCQAPFFKEITILKDYFNRSTSDVPNGGPLFLEILKNWK
Rabbit     -23 MSYTSYILAFQLCLILGSYGCYCQDTLTRETEHLKAYLKANTSDVANGGPLFLNILRNWK
Mouse      -22 MNATHCILALQLFLMAVS-GCYCHGTVIESLESLNNYFNSSGIDVEE-KSLFLDIWRNWQ
Rat        -22 MSATRRVLVLQLCLMALS-GCYCQGTLIESLGSLKNYFNSSSMDAMEGKSLLLDIWRNWQ

               *-**+*+***+***  *+* *****--  -* *-** ***+  +**+  * *** **+***
               *-**+*-***+ **  *+--*-* *+ ---*-*-** ***+*- **+ **+** -**+***
               *+** *-**+***  * --*-*** ----*-  ** *** *-+** -**+***-**+***
               *+**+*+***+****+ *+* *****-+- -* * ** *  + -+**+-**+*** **+***
               * -*  +**+** +-- * **** ++ ----*-* -***-*  ** - --***-*-+**-
               *+-*    * +****+-- * ******++----- -**-***-*- *  -*--* *-*-+**-

Human       38 EESDRKIMQSQIVSFYFKLFKNFKDDQSIQKSVETIKEDMNVKFFNSNKKKRDDFEKLTN
Bovine      38 DESDKKIIQSQIVSFYFKLFENLKDNQVIQRSMDIIKQDMFQKFLNGSSEKLEDFKKLIQ
Porcine     38 EESDKKIIQSQIVSFYFKFFEIFKDNQAIQRSMDVIKQDMFQRFLNGSSGKLNDFEKLIK
Rabbit      38 EESDNKIIQSQIVSFYFKLFDNLKDHEVIKKSMESIKEDIFVKFFNSNLTKMDDFQNLTR
Mouse       37 KDGDMKILQSQIISFYLRLFEVLKDNQAISNNISVIESHLITTFFSNSKAKKDAFMSIAK
Rat         38 KDGNTKILESQIISFYLRLFEVLKDNQAISNNISVIESHLITNFFSNSKAKKDAFMSIAK

               +*** ** ************ +-** * *+-* - **-*+ -+***--+ * ***-+*-
                ***-**+**************+*****-*+-*+- **-*++-+*-*-*- *- ** +*-
               +***-**+*********** ** -****+*+-*+-+**-*++- *-*-*- *- **-+*-+
               +*** **+************* +***  -* -*+- **-* +-+***--  * ***  *-
               ---* **-****-***--***-*****+*-----+*------ **--*+-*-*-*----+
               ---  **- ***-***--***-*****+*-----+*------ **--*+-*-*-*----+

Human       98 YSVTDLNVQRKAIHELIQVMAELSPAAKTGKRKRSQMLFRGRRASQ
Bovine      98 IPVDDLQIQRKAINELIKVMNDLSPKSNLRKRKRSQNLFRGRRASM
Porcine     98 IPVDNLQIQRKAISELIKVMNDLSPRSNLRKRKRSQTMFQGQRASK
Rabbit      98 ISVDDRLVQRKAVSELSNVLNFLSPKSNLKKRKRSQTLFRGRRASKY
Mouse       97 FEVNNPQVQRQAFNELIRVVHQLLPESSLRKRKRSRC
Rat         98 FEVNNPQIQHKAVNELIRVIHQLSPESSLRKRKRSRC

                -* ++ +*****+ *** *+  ***     ****** +*+*+***
               +-*+++*+*****++***-*++-***-*+******** +*+*+***
               +-*+++*+****+-***-*++-*** *+*********- * * ***-
               +-*++  +****--**  * + ***-*+* ******-+*+*+***-
               --*-+-*+** * +***-* --* *-*-*******--
               --*-+-*+* **-+***-* --***-*-*******--

               * = 4 or more matches
               + = 3 matches
               - = 2 matches
```

FIG. 15

DNA ENCODING NON-HUMAN ANIMAL INTERFERONS, VECTORS AND HOSTS THEREFOR, AND RECOMBINANT PRODUCTION OF IFN POLYPEPTIDES

CROSS REFERENCE TO RELATED APPLICATION

This is a divisional of application Ser. No. 07/949,327, filed Sep. 21, 1992; which is a continuation of application Ser. No. 07/749,371, filed Aug. 23, 1991, now abandoned; which is a continuation of application Ser. No. 07/104,461, filed Oct. 2, 1987, now abandoned; which is a continuation-in-part of application Ser. No. 06/438,128, filed Nov. 1, 1982, now abandoned; which is a continuation-in-part of application Ser. No. 06/355,298, filed Mar. 8, 1982, now abandoned.

FIELD OF THE INVENTION

The present invention relates generally to the field of recombinant DNA technology, to means and methods utilizing such technology in the discovery of a broad class of non-human animal interferons and to the production thereof and to the various products of such production and their uses.

More particularly, the present invention relates to the isolation and identification of DNA sequences encoding non-human animal interferons and to the construction of recombinant DNA expression vehicles containing such DNA sequences operably linked to expression-effecting promoter sequences and to the expression vehicles so constructed. In another aspect, the present invention relates to host culture systems, such as various microorganism and vertebrate cell cultures transformed with such expression vehicles and thus directed in the expression of the DNA sequences referred to above. In yet other aspects, this invention relates to the means and methods of converting the novel end products of such expression to entities, such as pharmaceutical compositions, useful for the prophylactic or therapeutic treatment of non-human animals. In addition, this invention relates to various processes useful for producing said DNA sequences, expression vehicles, host culture systems and end products and entities thereof and to specific and associated embodiments thereof.

The present invention arises in part from the discovery of the DNA sequence and deduced amino acid sequence encoding a series of bovine alpha interferons, including the 3'- and 5'-flanking sequences thereof facilitating their in vitro linkage into expression vehicles. These, in turn, enable the development of the means and methods for producing, via recombinant DNA technology, sufficient amounts of non-human animal interferons, so as to enable, in turn, the determination of their biochemical properties and bioactivity, making possible their efficient production for commercial/biological exploitation.

The publications and other materials hereof used to illuminate the background of the invention, and in particular cases, to provide additional details respecting its practice are hereby incorporated herein by this reference, and for convenience, are numerically referenced by the following text and respectively grouped in the appended bibliography.

BACKGROUND OF THE INVENTION

A. Non-human animal interferons

Interferon components have been isolated from tissues of various phylogenetic species lower than human (1,2,3). Activity studies conducted with these interferons have demonstrated varying degrees of antiviral effects in the requisite host animal (3,4,5,6). It also has been demonstrated that these interferons are not always species specific. For example, preparations of bovine interferons isolated from tissues, had antiviral activity on monkey and human cells (7). Likewise, human interferons have been found active in various cells of phylogenetically lower species (see 7).

This species interactivity is doubtless due to a high degree of homologous conservation, both in amino acid composition and sequence, amongst the interferons. However, until now, this explanation remained theoretical because the amounts and purities of non-human animal interferons that have been obtainable were insufficient to carry out unambiguous experiments on the characterization and biological properties of the purified components versus several of their human counterparts (8,9,10,11,12).

In any event, despite these low amounts and purities, a causal connection between interferon and anti-viral activity in the requisite animal host has been established. Thus, the production of non-human animal interferons in high yields and purities would be very desirable in order to initiate and successfully conduct animal bioassay experiments leading toward commercial exploitation in the treatment of animals for viral infections and malignant and immunosuppressed or immunodeficient conditions. In addition, the production of isolated non-human animal interferon species would enable their characterization, both physical and bioactive, and thus provide a basis for categorization and consequential comparative studies with counterpart human interferon species (see 8 to 20).

The studies done with non-human animal interferons, until the present invention, being restricted to the use of rather crude preparations, due to their very low availability, nevertheless suggest very important biological functions. Not only have the class of non-human animal interferons a potent associated therapeutic antiviral activity, but also potential as a prophylactic adjunct with vaccine and/or antibiotic treatment, clearly pointing to very promising clinical and commercial candidates.

It was perceived that the application of recombinant DNA technology would be a most effective way of providing the requisite larger quantities of non-human animal interferons necessary to achieve clinical and commercial exploitation. Whether or not the materials so produced would include glycosylation which is considered characteristic of native derived material, they would probably exhibit bioactivity admitting of their use clinically in the treatment of a wide range of viral, neoplastic, and immunosuppressed conditions or diseases in non-human animals.

B. Recombinant DNA Technology

Recombinant DNA technology has reached the age of some sophistication. Molecular biologists are able to recombine various DNA sequences with some facility, creating new DNA entities capable of producing copious amounts of exogenous protein product in transformed microbes. The general means and methods are in hand for the in vitro ligation of various blunt ended or "sticky" ended fragments of DNA, producing potent expression vehicles useful in transforming particular organisms, thus directing their efficient synthesis of desired exogenous product. However, on an individual product basis, the pathway remains somewhat tortuous and the science has not advanced to a stage where regular predictions of success can be made. Indeed, those who portend successful results without the underlying experimental basis, do so with considerable risk of inoperability.

The plasmid, an extrachromosomal loop of double-stranded DNA found in bacteria and other microbes, oftentimes in multiple copies per cell, remains a basic element of recombinant DNA technology. Included in the information encoded in the plasmid DNA is that required to reproduce the plasmid in daughter cells (i.e., an origin of replication) and ordinarily, one or more phenotypic selection characteristics such as, in the case of bacteria, resistance to antibiotics, which permit clones of the host cell containing the plasmid of interest to be recognized and preferentially grown in selective media. The utility of plasmids lies in the fact that they can be specifically cleaved by one or another restriction endonuclease or "restriction enzyme", each of which recognizes a different site on the plasmid DNA. Thereafter heterologous genes or gene fragments may be inserted into the plasmid by endwise joining at the cleavage site or at reconstructed ends adjacent to the cleavage site. Thus formed are so-called replicable expression vehicles. DNA recombination is performed outside the cell, but the resulting "recombinant" replicable expression vehicle, or plasmid, can be introduced into cells by a process known as transformation and large quantities of the recombinant vehicle obtained by growing the transformant. Moreover, where the gene is properly inserted with reference to portions of the plasmid which govern the transcription and translation of the encoded DNA message, the resulting expression vehicle can be used to actually produce the polypeptide sequence for which the inserted gene codes, a process referred to as expression.

Expression is initiated in a region known as the promoter which is recognized by and bound by RNA polymerase. In the transcription phase of expression, the DNA unwinds, exposing it as a template for initiated synthesis of messenger RNA from the DNA sequence. The messenger RNA is, in turn, translated into a polypeptide having the amino acid sequence encoded by the mRNA. Each amino acid is encoded by a nucleotide triplet or "codon" which collectively make up the "structural gene", i.e. that part which encodes the amino acid sequence of the expressed polypeptide product. Translation is initiated at a "start" signal (ordinarily ATG, which in the resulting messenger RNA becomes AUG). So-called stop codons define the end of translation and, hence, of production of further amino acid units. The resulting product may be obtained by lysing, if necessary, the host cell, in microbial systems, and recovering the product by appropriate purification from other proteins.

In practice, the use of recombinant DNA technology can express entirely heterologous polypeptides—so-called direct expression—or alternatively may express a heterologous polypeptide fused to a portion of the amino acid sequence of a homologous polypeptide. In the latter cases, the intended bioactive product is sometimes rendered bioinactive within the fused, homologous/heterologous polypeptide until it is cleaved in an extracellular environment (21, 22).

C. Cell Culture Technology

The art of cell or tissue cultures for studying genetics and cell physiology is well established. Means and methods are in hand for maintaining permanent cell lines, prepared by successive serial transfers from isolate normal cells. For use in research, such cell lines are maintained on a solid support in liquid medium, or by growth in suspension containing support nutriments. Scale-up for large preparations seems to pose only mechanical problems (See generally 23,24).

SUMMARY OF THE INVENTION

The present invention is based upon the discovery that recombinant DNA technology can be used to successfully produce non-human animal interferons, and each of them, preferably in direct form, and in amounts sufficient to initiate and conduct biological testing as prerequisites to market approval. The product is suitable for use, in all of its forms, in the prophylactic or therapeutic treatment of non-human animals, notably for viral infections and malignant and immunosuppressed or immunodeficient conditions. Its forms include various possible oligomeric forms which may include associated glycosylation as well as allelic or other, induced (such as via site directed mutagenesis of the underlying DNA) variations of individual members or family units. The products are produced by genetically engineered microorganisms or cell culture systems. Thus, the potential now exists to prepare and isolate non-human animal interferons in a more efficient manner than has been possible. One significant factor of the present invention, in its most preferred embodiment, is the accomplishment of genetically directing a microorganism or cell culture to produce a representative non-human animal interferon, bovine interferon, in isolatable amounts, produced by the host cell in mature form.

The present invention comprises the non-human animal interferons thus produced and the means and methods of their production. The present invention is further directed to replicable DNA expression vehicles harboring gene sequences encoding non-human animal interferons in expressible form. Further, the present invention is directed to microorganism strains or cell cultures transformed with the expression vehicles described above and to fermentation media comprising such transformed strains or cultures, capable of producing non-human animal interferons.

In still further aspects, the present invention is directed to various processes useful for preparing said interferon gene sequences, DNA expression vehicles, microorganism strains and cell cultures and to specific embodiments thereof. Still further, this invention is directed to the preparation of the fermentation media of said microorganisms and cell cultures. Further, in certain host systems, vectors can be devised to produce the desired non-human animal interferon, secreted from the host cell in mature form. The interferon containing the signal sequence derived from the 5'-flanking region of the gene proper is believed to be transported to the cellular wall of the host organisms where, aiding in such transport, the signal portion is cleaved during the secretion process of the mature interferon product. This embodiment enables the isolation and purification of the intended mature interferon without resort to involved procedures designed to eliminate contaminants of intracellular host protein or cellular debris.

In addition, this invention is specifically directed to the preparation of a bovine interferon representative of the class of non-human animal interferons embraced herein, produced by direct expression in mature form.

Reference herein to the expression "mature non-human animal interferon" connotes the microbial or cell culture production of non-human animal interferon unaccompanied by the signal peptide or presequence peptide that immediately attends translation of the non-human animal interferon mRNA. Mature non-human animal interferon, according to the present invention, is thus provided, having methionine as its first amino acid (present by virtue of the ATG start signal codon insertion in front of the structural gene) or, where the methionine is intra- or extracellularly cleaved, having its normally first amino acid. Mature non-human animal interferon can also be produced, in accordance herewith, together with a conjugated protein other than the conventional signal polypeptide, the conjugate being specifically cleavable in an intra- or extracellular environment (see 21). Finally, the mature non-human animal interferon can be produced by direct expression without the necessity of cleaving away any extraneous, superfluous polypeptide. This is particularly important where a given host may not, or not efficiently, remove a signal peptide where the expression vehicle is designed to express the mature interferon together with its signal peptide. The thus produced mature interferon is recovered and purified to a level fitting it for use in the treatment of viral, malignant, and immunosuppressed or immunodeficient conditions.

Non-human animal interferons hereof are those otherwise endogenous to the animal organism including, in nomenclature analogous to human interferons, animal alpha (leukocyte), beta (fibroblast) and gamma (immune) interferons. All three series have been identified in an animal model. Further, based upon the bovine example, the non-human animal alpha series is composed of a family of proteins as in the human case; those investigated have a lower degree of homology to the corresponding human alpha interferons than either those non-human animal interferons have amongst themselves or the human alpha interferons have amongst themselves. In addition, the bovine beta series is composed of a family of proteins, distinct from the human case. In addition, this invention provides interspecies and intrafamily hybrid interferons, by taking advantage of common restriction sites within the genes of the various non-human animal interferons hereof and recombining corresponding portions, according to known methods (see 57).

In any event, the non-human animal interferons embraced by this invention include those normally endogenous to animals of the avian, bovine, canine, equine, feline, hircine, ovine, piscine, and porcine families. In particular, the present invention provides interferons of cloven-hoofed animals such as cattle, sheep and goats. The interferons provided by this invention find application as antiviral and antitumor agents in the respective host animal. For example, bovine interferons would find practical applications in treating respiratory complex in cattle, either in conjunction with (per se known) antibiotics as a therapeutic component or with vaccines as a prophylactic component. Class utility, demonstrated as described above, would extend to other bovine, and to goats, sheep, pigs, horses, dogs, cats, birds and fish. In horses, dogs, cats and birds, the antitumor effect of the corresponding interferons could be expected to be especially important commercially.

Thus, for applications to particular host non-human animals, advantage can be taken in accordance herewith of demonstrated or otherwise manifest interspecies activity such that, for a given example, a given porcine interferon could find useful application in treating a bovine host. This may be particularly useful where, given a particular recombinant system or host according to the general ennoblement hereof, a particular interferon may be particularly susceptible to commercial exploitation whilst retaining essential bioactivity against a range of conditions not necessarily specific to the same family as that to which the given interferon belongs phylogenetically. In all events, such interspecies utility as can be determined according to analogous testing protocols is within the ambit of the present invention. See, for example, Ohman et al., *Antiviral Research* 7, 187 (1987) and the references cited therein, which are hereby incorporated by reference.

The following rationale, described with reference to bovine interferon as a representative of the class, may be employed for obtaining various non-human animal interferons hereof, in accordance with this invention:

1. Bovine tissues, for example bovine pancreas tissue, were reduced to frozen powder and treated to digest RNA and protein materials and provide, on precipitation, high molecular weight bovine DNA.
2. The high molecular weight DNA was partially digested for random cutting with respect to gene locus.
3. The resultant DNA fragments were size-fractionated giving from 15 to 20 kilo base pair fragments.
4. The resultant fragments of Step 3 were cloned using a λ Charon 30 phage vector.
5. The thus prepared vectors were packaged in vitro to infectious phage particles containing rDNA to provide a phage library. This was amplified by propagation on bacterial cells to about 106 fold. The phage were plated to virtual confluence on a lawn of bacteria and screened for hybridization with a radioactive human interferon probe.
6. From the appropriate clones the corresponding DNA was isolated and restriction mapped and analyzed by Southern hybridization. Restriction fragments containing bovine interferon genes were subcloned into plasmid vehicles and then sequenced.
7. The sequenced DNA was then tailored in vitro for insertion into an appropriate expression vehicle which was used to transform an appropriate host cell which was, in turn, permitted to grow in a culture and to express the desired bovine interferon product.
8. Bovine interferon thus produced has 166 amino acids in its mature form, beginning with cysteine, and 23 in the presequence, and is very hydrophobic in character. Its monomeric molecular weight has been calculated at about 21,409. It displays characteristics similar to human leukocyte interferons (8,9,10,11) and has been found to be about 60 percent homologous to a human leukocyte interferon.

Having isolated and identified the DNA encoding a particular non-human animal interferon in accordance herewith, it falls within the skill of the art as generally described and referenced herein to utilize that DNA as a sequence, or subsequence, useful to probe for other non-human interferons, of the same or different families, by application using the appropriate genomic library or other appropriate DNA source. Alternatively, synthetic probes of various lengths can be prepared based upon the sequence identified, or a genetically degenerate encoding form thereof, or the entire DNA sequence, could be synthesized according to contemporary skill in the art.

Having thus provided such DNA sequences, it similarly falls within the skill in the art, as generally described and referenced herein, to configure it in a number of equivalent expression systems for use with appropriate recombinant hosts.

Specific embodiments for such manipulations as described herein lay foundation, along with the extant art, for producing non-human animal interferons via a variety of enabled recombinant expression systems and hosts—vide supra. Likewise, it belongs to those skilled in the art of animal husbandry to test the thus produced interferons for bioactivity in members of the phylogenetically identical or equivalent families of non-human animals, the results of such bioactivity testing in turn confirming any interspecies and/or interfamilial utility.

DESCRIPTION OF PREFERRED EMBODIMENTS

A. Microorganisms/Cell Cultures

1. Bacterials Strains/Promoters

The work described herein was performed employing, inter alia the microorganism *E. coli* K-12 strain 294 (end A, $thi^-$, $hsr^-$, $_k hsm^+$) (25). This strain has been deposited with the American Type Culture Collection, ATCC Accession No. 31446. However, various other microbial strains are useful, including known *E. coli* strains such as *E. coli* B, *E. coli* X 1776 (ATCC No. 31537) and *E. coli* W 3110 (F−, λ−, protrophic) (ATCC No. 27325), *E. coli* DP 50 SuPF (ATCC No. 39061, deposited Mar. 5, 1982), *E. coli* JM83 (ATCC No. 39062, deposited Mar. 5, 1982) or other microbial strains many of which are deposited and (potentially) available from recognized microorganism depository institutions, such as the American Type Culture Collection (ATCC)—cf. the ATCC catalogue listing (See also 26, 26a). These other microorganisms include, for example, Bacilli such as *Bacillus subtilis* and other enterobacteriaceae among which can be mentioned as examples *Salmonella typhimurium* and *Serratia marcesans*, utilizing plasmids that can replicate and express heterologous gene sequences therein.

As examples, the beta lactamase and lactose promoter systems have been advantageously used to initiate and sustain microbial production of heterologous polypeptides. Details relating to the make-up and construction of these promoter systems can be obtained by reference to (27) and (28). More recently, a system based upon the tryptophan operon, the so-called trp promoter system, has been developed. Details relating to the make-up and construction of this system have been published by Goeddel et al. (12) and Kleid et al. (29). Numerous other microbial promoters have been discovered and utilized and details concerning their nucleotide sequences, enabling a skilled worker to ligate them functionally within plasmid vectors, have been published—see (30).

2. Yeast Strains/Yeast Promoters

The expression system hereof may also employ the plasmid YRp7 (31, 32, 33), which is capable of selection and replication in both *E. coli* and the yeast, *Saccharomyces cerevisiae*. For selection in yeast the plasmid contains the TRP1 gene (31, 32, 33) which complements (allows for growth in the absence of tryptophan) yeast containing mutations in this gene found on chromosome IV of yeast (34). One useful strain is strain RH218 (35) deposited at the American Type Culture Collection without restriction (ATCC No. 44076). However, it will be understood that any *Saccharomyces cerevisiae* strain containing a mutation which makes the cell trp1 should be an effective environment for expression of the plasmid containing the expression system. An example of another strain which could be used is pep4-1 (36). This tryptophan auxotroph strain also has a point mutation in TRP1 gene.

When placed on the 5' side of a non-yeast gene the 5'-flanking DNA sequence (promoter) from a yeast gene (for alcohol dehydrogenase 1) can promote the expression of a foreign gene in yeast when placed in a plasmid used to transform yeast. Besides a promoter, proper expression of a non-yeast gene in yeast requires a second yeast sequence placed at the 3'-end of the non-yeast gene on the plasmid so as to allow for proper transcription termination and polyadenylation in yeast. This promoter can be suitably employed in the present invention as well as others—see infra. In the preferred embodiments, the 5'-flanking sequence of the yeast 3-phosphoglycerate kinase gene (37) is placed upstream from the structural gene followed again by DNA containing termination—polyadenylation signals, for example, the TRP1 (31, 32, 33) gene or the PGK (37) gene.

Because yeast 5'-flanking sequence (in conjunction with 3' yeast termination DNA) (infra) can function to promote expression of foreign genes in yeast, it seems likely that the 5'-flanking sequences of any highly-expressed yeast gene could be used for the expression of important gene products. Since under some circumstances yeast expressed up to 65 percent of its soluble protein as glycolytic enzymes (38) and since this high level appears to result from the production of high levels of the individual mRNAs (39), it should be possible to use the 5'-flanking sequences of any other glycolytic genes for such expression purposes—e.g., enolase, glyceraldehyde—3-phosphate dehydrogenase, hexokinase, pyruvate decarboxylase, phosphofructokinase, glucose—6-phosphate isomerase, 3-phosphoglycerate mutase, pyruvate kinase, triosephosphate isomerase, phosphoglucose isomerase, and glucokinase. Any of the 3'-flanking sequences of these genes could also be used for proper termination and mRNA polyadenylation in such an expression system—cf. Supra. Some other highly expressed genes are those for the acid phosphatases (40) and those that express high levels of production due to mutations in the 5'-flanking regions (mutants that increase expression)—usually due to the presence of a TYl transposable element (41).

All of the genes mentioned above are thought to be transcribed by yeast RNA polymerase II (41). It is possible that the promoters for RNA polymerase I and III which transcribe genes for ribosomal RNA, 5S RNA, and tRNAs (41, 42), may also be useful in such expression constructions.

Finally, many yeast promoters also contain transcriptional control so they may be turned off or on by variation in growth conditions. Some examples of such yeast promoters are the genes that produce the following proteins: Alcohol dehydrogenase II, isocytochrome-c, acid phosphatase, degradative enzymes associated with nitrogen metabolism, glyceraldehyde—3-phosphate dehydrogenase, and enzymes responsible for maltose and galactose utilization (39). Such a control region would be very useful in controlling expression of protein product—especially when their production is toxic to yeast. It should also be possible to put the control region of one 5'-flanking sequence with a 5'-flanking sequence containing a promoter from a highly expressed gene. This would result in a hybrid promoter and should be possible since the control region and the promoter appear to be physically distinct DNA sequences.

3. Cell Culture Systems/Cell Culture Vectors

Propagation of vertebrate cells in culture (tissue culture) has become a routine procedure in recent years (see 43). The COS-7 line of monkey kidney fibroblasts may be employed as the host for the production of non-human animal interferons (44). However, the experiments detailed here could be performed in any cell line which is capable of the replication and expression of a compatible vector, e.g., WI38, BHK, 3T3, CHO, VERO, and HeLa cell lines. Additionally, what is required of the expression vector is an origin of replication and a promoter located in front of the gene to be expressed, along with any necessary ribosome binding sites, RNA splice sites, polyadenylation site, and transcriptional terminator sequences. While these essential elements of SV40 have been exploited herein, it will be understood that the invention, although described herein in terms of a preferred embodiment, should not be construed as limited to these sequences. For example, the origin of replication of other viral (e.g., Polyoma, Adeno, VSV, BPV, and so forth) vectors could be used, as well as cellular origins of DNA replication which could function in a nonintegrated state.

B. Vector Systems

1. Direct Expression of Mature Bovine Interferon in *E. coli*

The procedure used to obtain direct expression of bovine interferon in *E. coli* as a mature interferon polypeptide (minus signal sequence) involved the combination of a plasmid containing a promoter fragment and translational start signal with a tailored fragment of animal genomic DNA that contained the coding region for the mature interferon.

2. Expression in Yeast

To express a heterologous gene such as the DNA for non-human animal interferon in yeast, it is necessary to construct a plasmid vector containing four components. The first component is the part which allows for transformation of both *E. coli* and yeast and thus must contain a selectable gene from each organism, such as the gene for ampicillin resistance from *E. coli* and the gene TRP1 from yeast. This component also requires an origin of replication from both organisms to be maintained as a plasmid DNA in both organisms, such as the *E. coli* origin from pBR322 and the ars1 origin from chromosome III of yeast.

The second component of the plasmid is a 5'-flanking sequence from a highly expressed yeast gene to promote transcription of a downstream-placed structural gene, such as the 5'-flanking sequence used is that from the yeast 3-phosphoglycerate kinase (PGK) gene.

The third component of the system is a structural gene constructed in such a manner that it contains both an ATG translational start and translational stop signals. The isolation and construction of such a gene is described infra.

The fourth component is a yeast DNA sequence containing the 3'-flanking sequence of a yeast gene, which contains the proper signals for transcription termination and polyadenylation.

3. Expression in Mammalian Cell Culture

The strategy for the synthesis of immune interferon in mammalian cell culture relies on the development of a vector capable of both autonomous replication and expression of a foreign gene under the control of a heterologous transcriptional unit. The replication of this vector in tissue culture can be accomplished by providing a DNA replication origin (derived from SV40 virus), and providing helper function (T antigen) by the introduction of the vector into a cell line endogenously expressing this antigen (46, 47). The late promoter of SV40 virus preceded the structural gene of interferon and ensured the transcription of the gene.

A useful vector to obtain expression consists of pBR322 sequences which provides a selectable marker for selection in *E. coli* (ampicillin resistance) as well as an *E. coli* origin of DNA replication. These sequences are derived from the plasmid pML-I (46) and encompasses the region spanning the EcoRI and BamHI restriction sites. The SV40 origin is derived from a 342 base pair PvuII-HindIII fragment encompassing this region (48, 49) (both ends being converted to EcoRI ends). These sequences, in addition to comprising the viral origin of DNA replication, encode the promoter for both the early and late transcriptional unit. The orientation of the SV40 origin region is such that the promoter for the late transcriptional unit is positioned proximal to the gene encoding interferon.

BRIEF DESCRIPTION OF THE DRAWINGS

FIGS. 3A-1 and 3A-2 shows a portion of the nucleotide sequence from the plasmid subclone p83BamHI1.9kb as well as the deduced amino acid sequence for the bovine leukocyte interferon coded therein. The signal peptide is represented by amino acid residues S1 through S23.

FIGS. 3B-1 and 3B-2 shows the nucleotide sequence and deduced amino acid sequence for a second bovine leukocyte interferon (α2) from the plasmid subclone p67EcoRI 3.2 kb.

FIGS. 3C-1 and 3C-2 shows the complete mature nucleotide sequence and deduced amino acid-sequence for a third bovine leukocyte interferon (α3) from the plasmid subclone p35EcoRI-BamHI 3.5 kb.

FIGS. 3D-1 and 3D-2 shows the nucleotide sequence and deduced amino acid sequence for a fourth bovine leukocyte interferon hereof from the plasmid subclone p83EcoRI-BamHI 2.9 kb. The signal is represented by amino acid residues SI to S23. The mature protein comprises 172 amino acid residues. It is noted that the last stretch of six amino acid residues is attributed to a nucleotide base change at position 511 which allows six additional translatable codons before the next in phase stop signal.

FIGS. 4A, 4B and 4C compare the amino acid sequences of BoIFN-α1, α2, α3 and α4 with the sequences for 11 known human leukocyte interferons. Also given are the amino acids conserved among all human leukocyte interferons, all bovine leukocyte interferons, and with respect to bovine α1 and α4, positions where homology with the majority of human leukocyte interferons occur.

FIGS. 9A-1 and A2, 9B-1 and B-2, and 9C-1 and C-2 depict the nucleotide and deduced amino acid sequences for the BoIFN-β1, 2 and 3 genes.

FIG. 10 compares the amino acid sequences for the three BoIFN-βs with HuIFN-β.

FIG. 13 gives the comparison of the deduced amino acid sequences of BoIFN-γ, HuIFN-γ and murine IFN-γ.

FIGS. 14A–14E depict the complete nucleotide and deduced amino acid sequence of the porcine IFN-α1, porcine IFN-β1, porcine-γ, feline IFN-β1 and rabbit IFN-γ genes.

FIG. 15 shows the homologies from amongst the human, bovine, porcine, rabbit, mouse and rat IFN-γ interferons. Letters are in accordance with the standard assignments for amino acids as follows:

Figure 1:
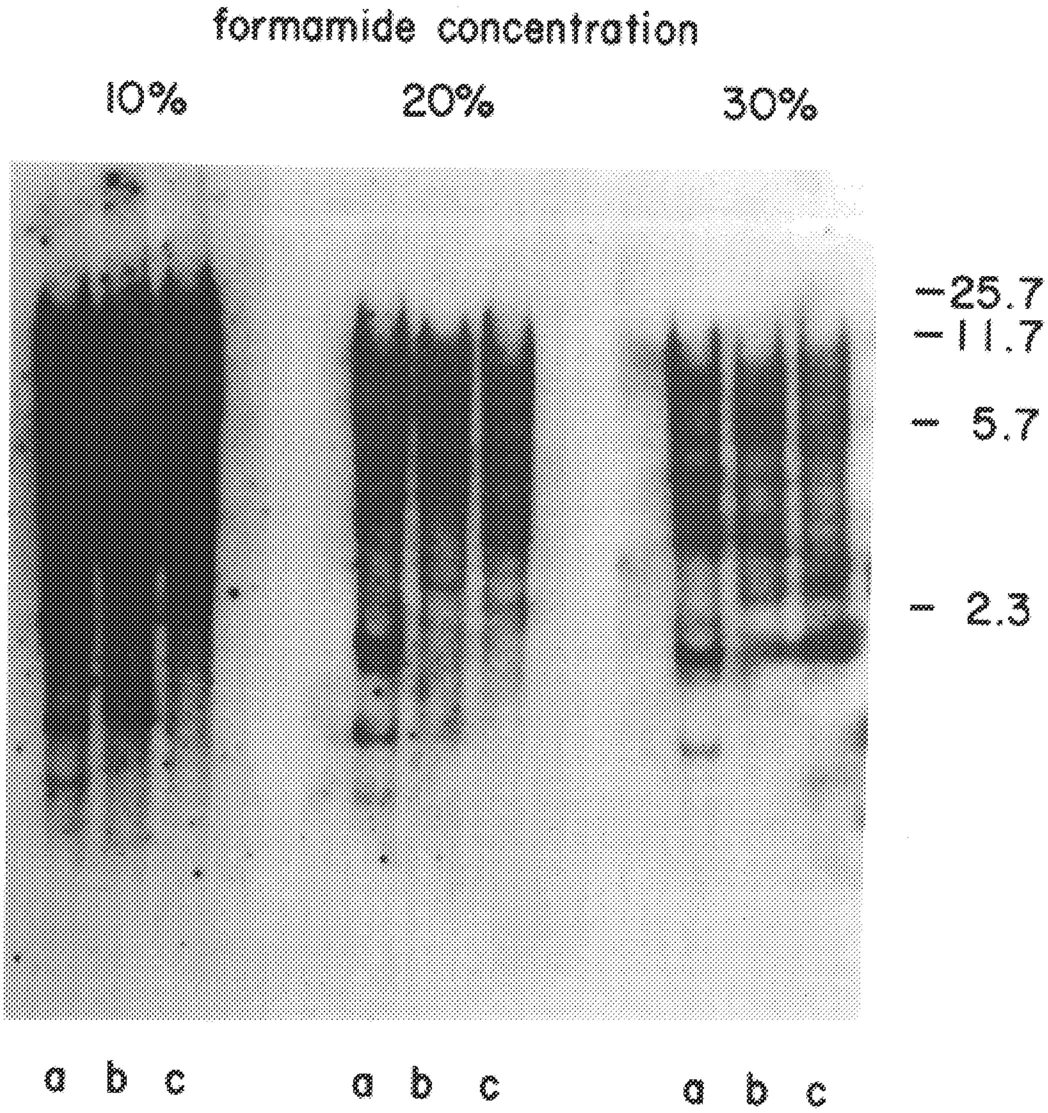
FIG. 1 depicts a Southern hybridization of (a) human, (b) bovine and (c) porcine genomic DNAs digested with EcoRI and hybridized at different formamide concentrations with a $^{32}$p-labelled 570 base-pair EcoRI fragment containing the coding region of the human leukocyte interferon A/D hybrid. The hybridization at 20 percent formamide gives the clearest pattern of the multigene bovine and porcine leukocyte interferon gene families.

| | | | | | |
|---|---|---|---|---|---|
| Asp | D | Aspartic acid | Ile | I | Isoleucine |
| Thr | T | Threonine | Leu | L | Leucine |
| Ser | S | Serine | Tyr | Y | Tyrosine |
| Glu | E | Glutamic acid | Phe | F | Phenylalanine |
| Pro | P | Proline | His | H | Histidine |
| Gly | G | Glycine | Lys | K | Lysine |
| Ala | A | Alanine | Arg | R | Arginine |
| Cys | C | Cysteine | Trp | W | Tryptophan |
| Val | V | Valine | Gln | Q | Glutamine |
| Met | M | Methionine | Asn | N | Asparagine |

DETAILED DESCRIPTION

The following detailed description is illustrative of the invention for the preparation, via recombinant DNA technology, of the various non-human animal interferons embraced, and sets forth generally applicable methodology for the preparation of particular, bovine leukocyte interferons. The method is described with respect to a bacterial system.

A. Isolation of Bovine DNA

For the purpose of constructing an animal gene library, high molecular weight DNA was isolated from animal tissue by a modification of the Blin and Stafford procedure (50), randomly fragmented with respect to gene locus, and size fractionated to obtain 15–20 kilobase fragments for cloning into a lambda phage vector (51).

Frozen tissue, for example bovine pancreas, was ground to a fine powder in liquid nitrogen and solubilized in 0.25M EDTA, 1 percent Sarkosyl, 0.1 mg/ml Proteinase K (25 ml/gram tissue) at 50° C. for 3 hours. The viscous solution obtained was deproteinized by three phenol and one chloroform extractions, dialysed against 50 mM Tris-HCl (pH8), 10 mM EDTA, 10 mM NaCl and digested with heat-treated pancreatic ribonuclease (0.1 mg/ml) for 2 hours at 37° C. After phenol and ether extraction, the DNA was precipitated with two volumes of ethanol, washed in 95 percent ethanol, lyophilized and redissolved in TE buffer (10 mM Tris-HCl (pH 7.5), 1 mM EDTA) overnight at 4° C. at a final concentration of 1–2 mg/ml. The final DNA preparation was greater than 100 kilobases in length as determined by electrophoresis on a 0.5 percent neutral agarose gel.

B. Partial Endonuclease Digestion and Size Fractionation of Bovine DNA

Aliquots (0.1 mg) of bovine DNA were digested with 1.25, 2.5, 5 and 10 units of Sau3A at 37° C. for 60 minutes in a reaction (1 ml) containing 10 mM Tris-HCl (pH 7.5), 10 mM MgC12, 2 mM dithiothreitol. Incubations were stopped by adding EDTA to 25 mM, phenol and ether extracted, made 0.3M in sodium acetate (pH 5.2) and precipitated with 3 volumes of ethanol. The DNA was redissolved in TE buffer at 68° C. and sedimented through a 10–40 percent linear sucrose gradient (51) in a Beckman SW 27 rotor at 27,000 rpm for 22 hours at 20° C. Fractions (0.5 ml) were analyzed on a 0.5 percent gel using Eco R1-digested Charon 4A (51a) DNA as a molecular weight standard. Those fractions containing 15–20 kilobase DNA fragments were combined, precipitated with ethanol and redissolved in TE buffer.

C. Construction of the Bovine Genomic DNA Library

The 15–20 kb bovine DNA nonlimit digest was cloned into a lambda Charon 30 A vector (52) having G-A-T-C sticky ends generated by removal of the two internal Bam HI fragments of the phage. Charon 30 A was grown in *E. coli* strain DP 50 SupF (ATTC No. 39061, deposited Mar. 5, 1982) in NZYDT broth, concentrated by polyethylene glycol precipitation and purified by CsCl density gradient centrifugation (53). Phage DNA was prepared by extracting the purified phage twice with phenol, once with phenol and ether, and concentrating the DNA by ethanol precipitation.

For preparation of the end fragments of Charon 30 A, 50 micrograms of phage DNA was annealed for 2 hours at 42° C. in 0.25 ml of 50 mM Tris-HCl (pH 8), 10M NaCl, digested to completion with Bam HI, phenol and ether extracted, and sedimented through a 10 to 40 percent sucrose gradient as described above. Fractions containing the 32 kb annealed arms of the phage were combined and ethanol precipitated.

The purified Charon 30 A arms (6 micrograms) were reannealed at 42° C. for 2 hours, combined with 0.3 micrograms of 15–20 kb bovine DNA an 400 units of phage T4 polynucleotide ligase and incubated overnight at 12° C. in a 0.075 ml reaction containing 50 mM Tris-HCl (pH 7.5), 10 mM MgC12, 20 mM dithiothreitol and 50 micrograms/ml bovine serum albumin. The ligated DNA mixture was then packaged into mature lambda phage particles using an in vitro lambda packaging system (54).

The components of this system-sonic extract (SE), freeze-thaw lysate (FTL), protein A, and buffers A and M1-were prepared as described (54). Three microliter aliquots of the ligated DNA mixture were incubated with 15 microliters of Buffer A, 2 microliters of Buffer M1, 10 microliters of SE and 1 microliter of protein A for 45 minutes at 27° C. The FTL was thawed on ice for 45 minutes, combined with 0.1 volumes of Buffer M1, centrifuged at 35,000 rpm at 4° C. for 25 minutes, and 0.075 ml aliquots of the supernatant were added to the above reaction. After an additional 2 hours of incubation at 27° C., a small aliquot of the packaging reaction was titered on strain DP 50 SupF, supra. This procedure yielded a total of approximately $1.1\times10^6$ independent bovine DNA recombinants. The remainder of the packaging mixture was amplified by a plate-lysate method (52) by plating out the recombinants on DP 50 SupF at a density of 10,000 plaque-forming units per 15 cm NZYDT agar plate.

D. Screening of the Phage Library for Bovine Interferon Genes

The strategy used to identify phage recombinants carrying bovine interferon genes consisted in detecting nucleotide homology with radioactive probes prepared from cloned human leukocyte (8,9), fibroblast (12) and immune (55) interferon genes. Hybridization conditions were established with Southern blots (56) of genomic animal DNA. Five micrograms each of high molecular weight DNA (prepared as described above) from human placenta, bovine pancreas and pig submaxillary gland were digested to completion with Eco RI, electrophoresed on a 0.5 percent agarose gel and transferred to nitrocellulose paper (56). A 32P-labelled DNA probe was prepared from a 570 base-pair Eco R1 fragment containing the protein coding region of the mature human leukocyte interferon A/D hybrid at the Bgl II restriction site (57) by standard procedures (58). Each nitrocellulose filter was rehybridized at 42° C. overnight in 5×SSC (56), 50 mM sodium phosphate (pH 6.5), 0.1 mg/ml sonicated salmon sperm DNA, 5× Denhardt's solution (59), 0.1 percent sodium dodecyl sulfate, 0.1 percent sodium pyrophosphate that contained either 10 percent, 20 percent, or 30 percent formamide, and then hybridized with $100\times10^6$ counts per minute of the labelled probe in the same solution containing 10 percent sodium dextran sulfate (60). After an overnight incubation at 42° C., the filters were washed 4 times in 2×SSC, 0.1 percent SDS at room temperature, once in 2×SSC and then exposed to Kodak XR-5 x-ray film with Dupont Cronex intensifying screens overnight. As seen in FIG. 1, a number of hybridizing bands are most readily detected in the bovine and porcine DNA digests when 20 percent formamide is present in the hybridization. This result provides evidence for a multigene family of leukocyte interferon genes in cow and pig analogous to that previously demonstrated in humans (12,61). The same hybridization conditions were therefore employed to screen for interferon genes in the bovine DNA library.

500,000 recombinant phage were plated out on DP 50 SupF at a density of 10,000 pfu/15 cm plate, and duplicate nitrocellulose filter replicas were prepared for each plate by the method of Benton and Davis (62). The filters were hybridized with the human LeIF gene probe as described above. Ninety-six duplicate hybridizing plaques were obtained which gave strong signals upon repeated screening.

The bovine library was further screened for fibroblast and immune interferon genes. Probes were made from a 502 base-pair Xba I-Bgl III fragment containing the entire mature human fibroblast interferon gene (12), and a 318 base-pair Alu I fragment (containing amino acids 12–116) and 190 base-pair Mbo II fragment (containing amino acids 99–162) from the mature coding region of the human immune interferon gene (55). Hybridization of $1.2\times10^6$ recombinant phage yielded a total of 26 bovine fibroblast and 10 bovine immune interferon clones.

E. Characterization of the Recombinant Phage

Figure 2:
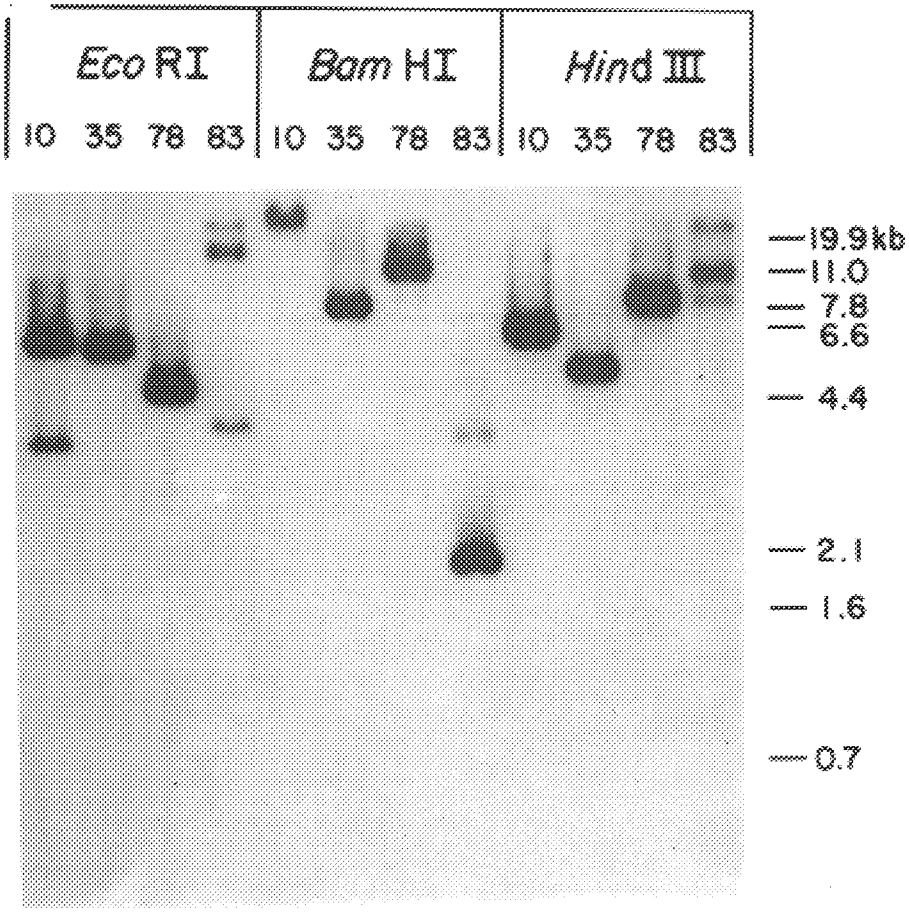
FIG. 2 depicts a Southern hybridization of four different bovine genomic DNA phage recombinants digested with EcoRI, BamHI or HindIII and hybridized with a 32P-labelled human leukocyte gene probe. Clone 83 yields two hybridizing fragments with each restriction enzyme.

Phage DNA was prepared (as described above) from 12 recombinants which hybridized with the human leukocyte interferon probe. Each DNA was digested singly and in combination with Eco R1, Bam HI and Hind III, electrophoresed on a 0.5 percent agarose gel and the location of the hybridizing sequence mapped by the Southern method (56). A comparison of singly digested DNA from clones 10, 35, 78 and 83 is shown in FIG. 2. For each phage the sizes of restriction fragments observed as well as the corresponding hybridization pattern is distinct and nonoverlapping, suggesting that each of these four phage carry a different bovine interferon gene. In addition, digestion of clone 83 with each of the three enzymes yields in each case two discrete hybridizing bands, indicating that this recombinant may carry two closely linked interferon genes.

F. Subcloning of the Bovine Leukocyte Interferon Genes

Restriction fragments from three of the recombinant phage which hybridized with the human leukocyte gene probe were subclones into the multiple restriction enzyme cloning site of the pBR322 derivative, pUC9. The plasmid pUC9 was derived from pBR322 by first removing the 2,067 base-pair EcoRI-PvuII fragment containing the tetracycline resistance gene, then inserting a 425 base-pair HaeII fragment from the phage M13 derivative mP9 (62a) into the HaeII site of the resulting plasmid at position 2352 (relative to the pBR322 notation). The HaeII fragment from mp9 contains the N-terminal coding region of the *E. coli* lacZ gene in which a multi-restriction enzyme cloning site of the sequence, CCAAGC TTG GCT GCA GGT CGA CGG ATC CCC GGG, has been inserted between the 4th and 5th amino acid residues of β-galactosidase. Insertion of a foreign DNA fragment into these cloning sites disrupts the continuity between the lac promoter and lacZ gene, thus altering the phenotype of a JM83 transformed with the plasmid from $lac^+$to $lac^-$.

The fragments referred to above were: (a) a 1.9 kb Bam HI fragment and 3.7 kb EcoRI fragment from clone 83 (which corresponds to nonoverlapping segments of the same recombinant), (b) a 3.5 kb BamHI-EcoRI fragment from clone 35, and (c) a 3.2 kb EcoRI fragment from clone 67. In each case, 0.1 micrograms of the appropriately digested vector was ligated with a tenfold molar excess of the purified fragment, transformed *E. coli* strain JM83 (ATCC No. 39062, deposited Mar. 5, 1982), plated out onto M9 (63) plates containing 0.04 mg/ml 5-bromo-4-chloro-3-indolyl-β-D-galactoside and 0.2 mg/ml ampicillin. White colonies, which presumably carry a DNA insert at a restriction site interrupting the coding region of the lacZ gene on pUC9, were picked into 5 ml of LB broth plus 0.02 mg/ml ampicillin, grown for several hours at 37° C., and screened for the inserted fragment by a plasmid DNA minipreparation procedure (64.)

G. DNA Sequence of a Bovine Leukocyte Interferon Gene on Clone 83

Figure 4C:
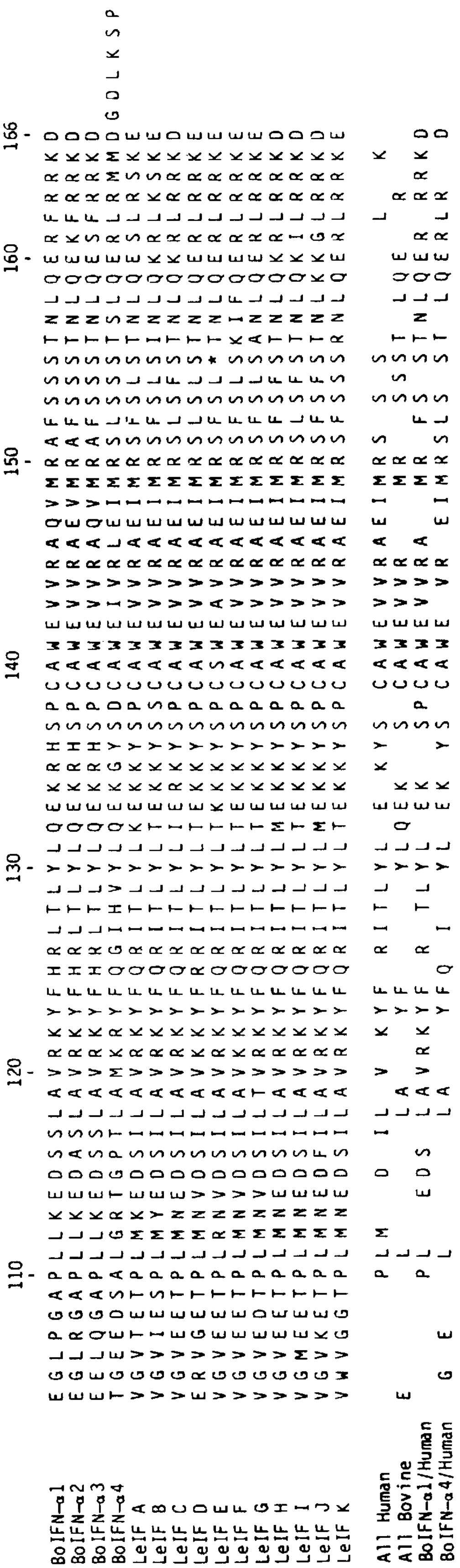

The DNA sequence extending from the Bam HI site of p83BamHI1.9kb (the 1.9 kb fragment subclone of clone 83) was determined by the Maxam-Gilbert chemical procedure (65), and is presented in FIG. 3. The longest open reading frame encodes a polypeptide of 189 amino acids with significant homology to the human leukocyte interferons (FIG. 4). By analogy with the human proteins, the bovine leukocyte interferon consists of a hydrophobic 23 amino acid signal peptide which precedes a 166 amino acid mature protein by an identical sequence, ser-leu-gly-cys. Four cysteine residues at positions 1, 29, 99 and 139 are exactly conserved between species. A pairwise homology comparison between the bovine and human interferons is shown in Table 1. As may be expected, the bovine protein is significantly less homologous—(approximately 60 percent) to each of the human proteins than the latter are to one another (greater than 80 percent).

The DNA sequence and deduced amino acid sequence for three additional bovine leukocyte interferon genes occurring on the plasmid subclones p67EcoRI 3.2 kb, p35EcoRI-BamHI 3.5 kb and p83EcoRI 3.7 kb are shown in FIGS. 3B, 3C and 3D, respectively.

As summarized in Table 1, whereas the BoIFN-α2 and 3 genes encode peptides with only minor apparent differences to BoIFN-α1, the BoIFN-α4 protein is as distinct from the other bovine peptides as are any two bovine and human leukocyte interferons.

Figure 6:
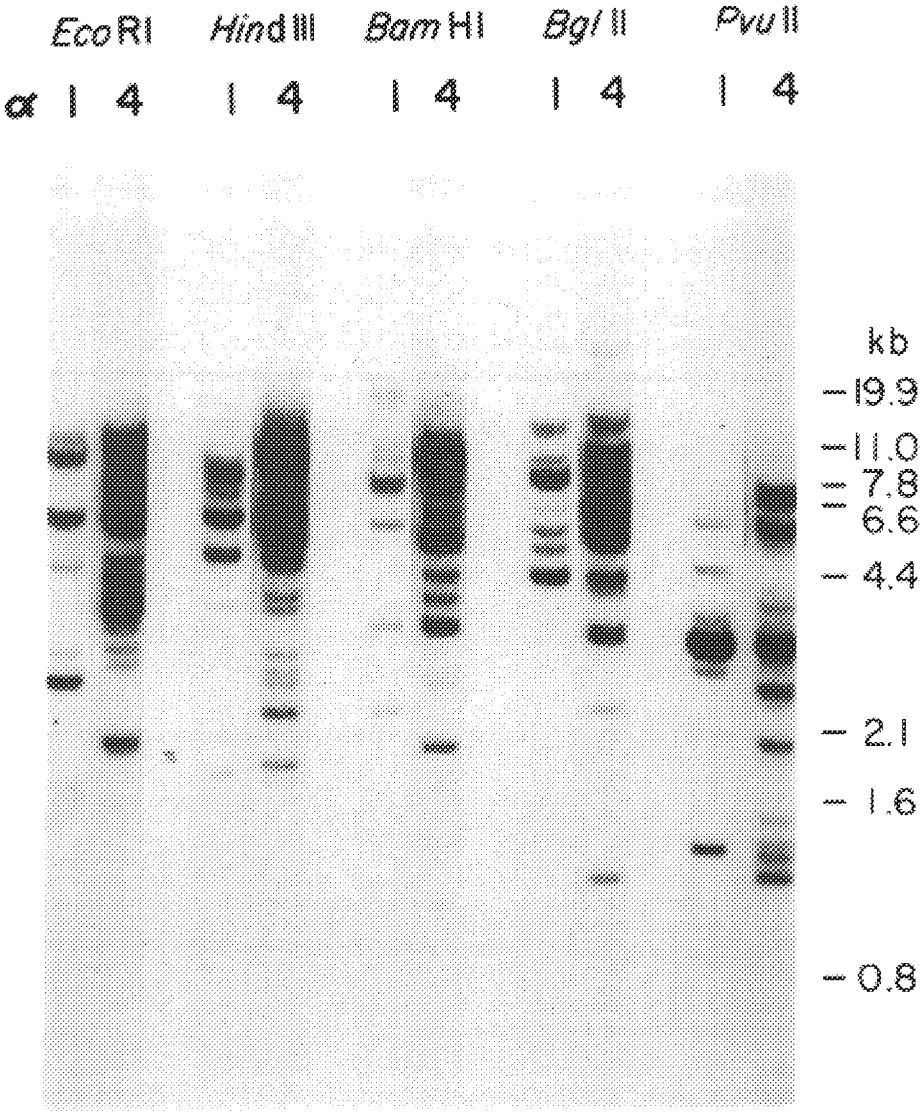
FIG. 6 depicts a Southern hybridization of bovine DNA digested with either EcoRI, HindIII, BamHI, BglII and PvuII with a radioactive probe prepared from BoIFN-αI or BoIFN-α4 gene fragments. Each IFN gene preferentially hybridizes with a distinct subfamily of BoIFN-α genes.

To ascertain whether the α4 gene derives from as broad a class of cellular proteins as the other BoIFN-αs, genomic bovine DNA was digested with several restriction endonucleases and hybridized with radioactive DNA fragments representing the protein coding regions of the α1 (612 bp AvaII fragment, FIG. 6) and α4 (EcoRI-XmnI fragment of pBoIFN-α4trp15) genes, under conditions of high stringency (50 percent formamide) that do not allow cross hybridization of the two genes. As seen in FIG. 6, each gene preferentially hybridizes to a distinct set of bovine DNA fragments. These results together clearly demonstrate the existence of two different families of bovine leukocyte IFN peptides, of which the α1 and α4 proteins may be thought of as representative members.

TABLE 1

Pairwise comparisons of differences in coding sequences of bovine and human IFN-αs

| | α1 | α2 | α3 | α4 | αA | αB | αC | αD | αF | αH | αI | αJ | αK |
|---|---|---|---|---|---|---|---|---|---|---|---|---|---|
| BoIFN-α1 | | 94 | 92 | 54 | 61 | 62 | 63 | 64 | 61 | 64 | 63 | 61 | 65 |
| BoIFN-α2 | 96 | | 91 | 53 | 61 | 61 | 64 | 63 | 62 | 63 | 63 | 64 | 64 |
| BoIFN-α3 | 100 | 96 | | 45 | | | | | | | | | |
| BoIFN-α4 | 52 | 48 | 52 | | 54 | 54 | 58 | 55 | 56 | 58 | 56 | 54 | 54 |
| HuIFN-αA | 56 | 52 | | 39 | | 81 | 81 | 83 | 82 | 83 | 81 | 80 | 86 |
| HuIFN-αB | 43 | 39 | | 48 | 70 | | 81 | 77 | 81 | 83 | 80 | 79 | 81 |
| HuIFN-αC | 61 | 57 | | 52 | 70 | 65 | | 81 | 89 | 86 | 94 | 92 | 83 |
| HuIFN-αD | 52 | 48 | | 48 | 74 | 61 | 65 | | 83 | 81 | 80 | 78 | 84 |
| HuIFN-αF | 61 | 57 | | 52 | 70 | 65 | 100 | 65 | | 83 | 89 | 86 | 83 |
| HuIFN-αH | 56 | 52 | | 52 | 74 | 74 | 74 | 83 | 74 | | 84 | 84 | 84 |
| HuIFN-αI | 61 | 57 | | 52 | 70 | 65 | 100 | 65 | 100 | 74 | | 91 | 81 |
| HuIFN-αJ | 56 | 52 | | 48 | 61 | 57 | 91 | 70 | 91 | 65 | 91 | | 80 |
| HuIFN-αK | 52 | 48 | | 48 | 83 | 70 | 74 | 91 | 74 | 91 | 74 | 65 | |

Numbers represent percentage homology
Lower-left half represents 23 acid presequence
Upper-right half represents 166 acid mature protein
A,B,C, etc. are human leukocyte interferons A,B,C, etc.

H. Direct Expression of Mature BoIFN-αI in *E. coli*

Figure 5:
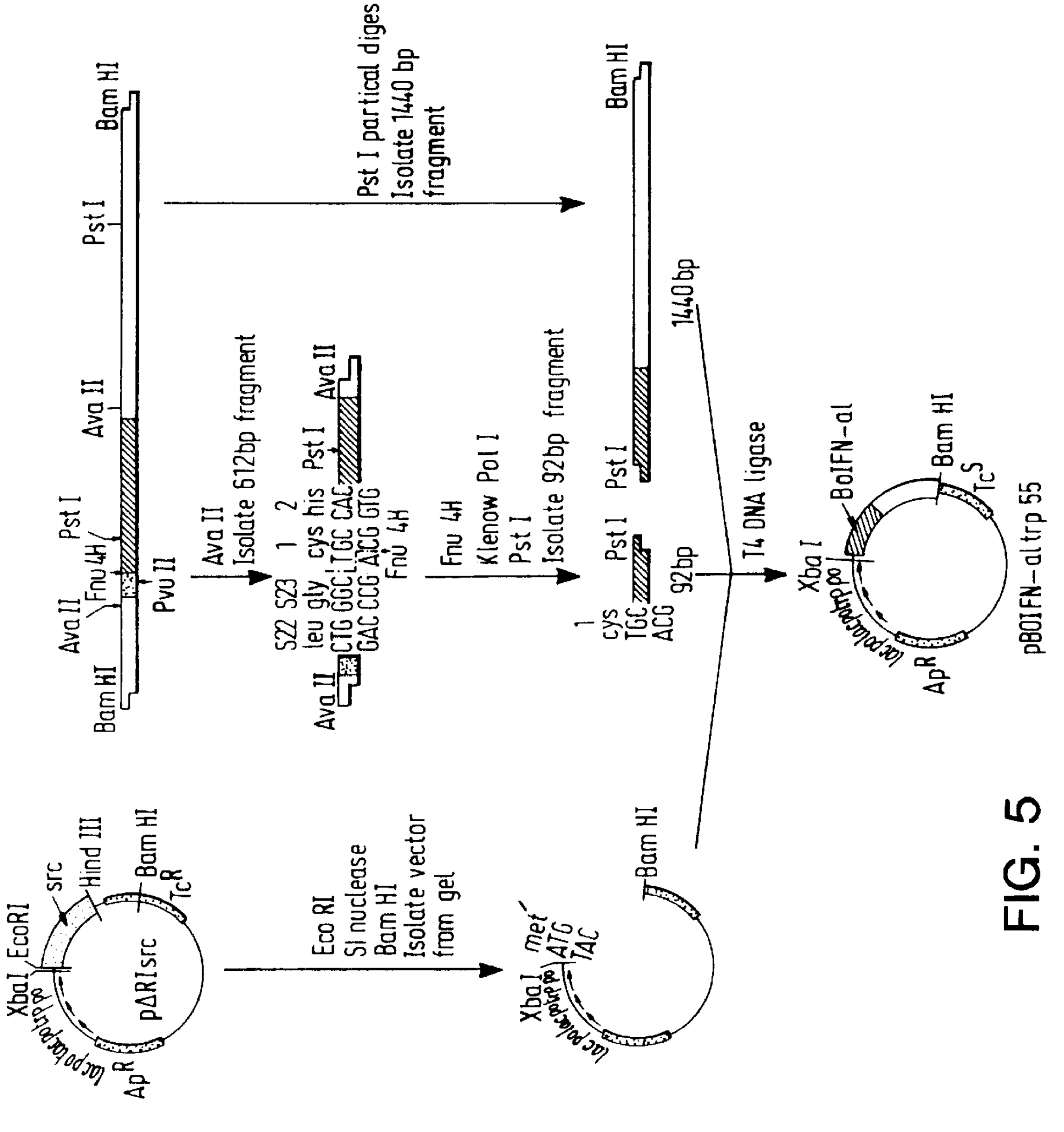
FIG. 5 is a schematic diagram of the construction of the bovine leukocyte interferon expression plasmid pBoIFN-α1trp55. The starting materials are the trp expression vector pdeltaRIsrc and the BamHI fragment from the plasmid subclone p83BamHI1.9kb.

The construction of the direct expression plasmid is sunmarized in FIG. 5. The plasmid subclone p83BamHI1.9kb was digested to completion with Ava II, and the 612 base-pair fragment containing the bovine leukocyte interferon gene isolated by electrophoresis on a 6 percent polyacrylamide gel and electroeluted. Approximately 1.5 micrograms of this fragment was digested with Fnu4H, phenol and ether extracted, and ethanol precipitated. The resulting Fnu4H sticky ends were extended to blunt ends with 6 units of DNA polymerase 1 (Klenow fragment) at 12° C. for 30 minutes in 20 microliters containing 20 mM Tris-HCl (pH 7.5), 10 mM $MgCl_2$, 4 mM dithiothreitol and 0.1 mM each dATP, dGTP, dCTP and dTTP. After extraction with phenol and ether, the DNA was digested with Pst I and electrophoresed on a 6 percent gel. The resulting 92 base-pair blunt end-Pst I fragment which extends from the first nucleotide of the coding region for the mature bovine leukocyte interferon was electroeluted from the gel.

The remainder of the mature coding region was isolated as follows. Three micrograms of the Bam HI insert of p83BamHI1.9kb was partially digested with 14 units of Pst I for 10 minutes at 37° C. in a 45 microliter reaction containing 10 mM Tris-HCl (pH 7.5), 10 mM $MgCl_2$, 2 mM dithiothreitol, and extracted with phenol and ether. The desired 1440 base-pair partial Pst I-Bam HI fragment extending from nucleotide 93 of the mature coding region was isolated from a 6 percent polyacrylamide gel.

The plasmid pdeltaRIsrc is a derivative of the plasmid pSRCex16 (66) in which the Eco RI sites proximal to the trp promoter and distal to the src gene have been removed by repair with DNA polymerase 1 (67), and the self-complementary oligodeoxynucleotide AATTATGAATTCAT (synthesized by the phosphotriester method (68)) was inserted into the remaining Eco RI site immediately adjacent to the Xba I site. 20 micrograms of pdeltaRIsrc was digested to completion with Eco RI, phenol and ether extracted, and ethanol precipitated. The plasmid was then digested with 100 units of nuclease S1 at 16° C. for 30 minutes in 25 mM sodium acetate (pH 4.6), 1 mM $ZnC1_2$ and 0.3M NaCl to create a blunt end with the sequence ATG. After phenol and ether extraction and ethanol precipitation, the DNA was digested with Bam HI, electrophoresed on a 6 percent polyacrylamide gel, and the large (4300 bp) vector fragment recovered by electroelution.

The expression plasmid was assembled by ligating together 0.2 micrograms of vector, 0.02 micrograms of the 92 bp blunt-Pst I fragment and 0.25 micrograms of the 1400 bp partial Pst I—Bam HI fragment with 400 units of T4 DNA ligase overnight at 12° C., and used to transform *E. coli* strain 294 (ATCC No. 31446) to ampicillin resistance. Plasmid DNA was prepared from 96 of the colonies and digested wit Xba 1 and Pst I. Nineteen of these plasmids contained the desired 103 base-pair XbaI-PstI and 1050 base-pair Pst 1 fragments. DNA sequence analysis verified that several of these plasmids had an ATG initiation codon correctly placed at the start of the bovine interferon coding region. One of these plasmids, pBoIFN-α1trp55 was chosen for further study.

I. Direct Expression of a Second Class of Mature Bovine Leukocyte Interferon (α-4) in *E. coli*

An ATG initiation codon was placed in front of the mature coding region by the enzymatic extension of a synthetic DNA primer, CATGTGTGACTTGTCT. The heptadecamer was phosphorylated with T4 polynucleotide kinase and γ-32P ATP as previously described (12). 250 pmoles of the primer was combined with approximately 1 microgram of a 319 bp HincII fragment containing amino acid residues S20 to 102 in 30 microliters of $H_2O$, boiled for 5 min, and extended with 25 units of *E. coli* DNA polymerase I Klenow fragment at 37° C. for 3 hours. The product of this reaction was digested with HgiAI and the resulting 181 bp blunt-HgiAI fragment was isolated from a 6 percent polyacrylamide gel.

The entire gene for the mature peptide was assembled behind the trp promoter by enzymatically ligating the above fragment with a 508 bp HgiA-PstI fragment containing the carboxy-terminal portion of the peptide and the HuIFN-γ expression plasmid, pIFN-γtrp48-13 (55), which had been digested with EcoRI, extended to flush ends with Klenow DNA polymerase, digested with PstI and finally isolated on a 6 percent polyacrylamide gel. Upon transformation of resulting mixture into *E. coli* 294, several clones were identified which had restored the EcoRI recognition site between the trp promoter-ribosome binding site region of the parent expression vector and the complete coding region of the mature bovine IFN (pBoIFN-α4trp15).

J. Subcloning of the Bovine Fibroblast Interferon Genes

Figure 7:
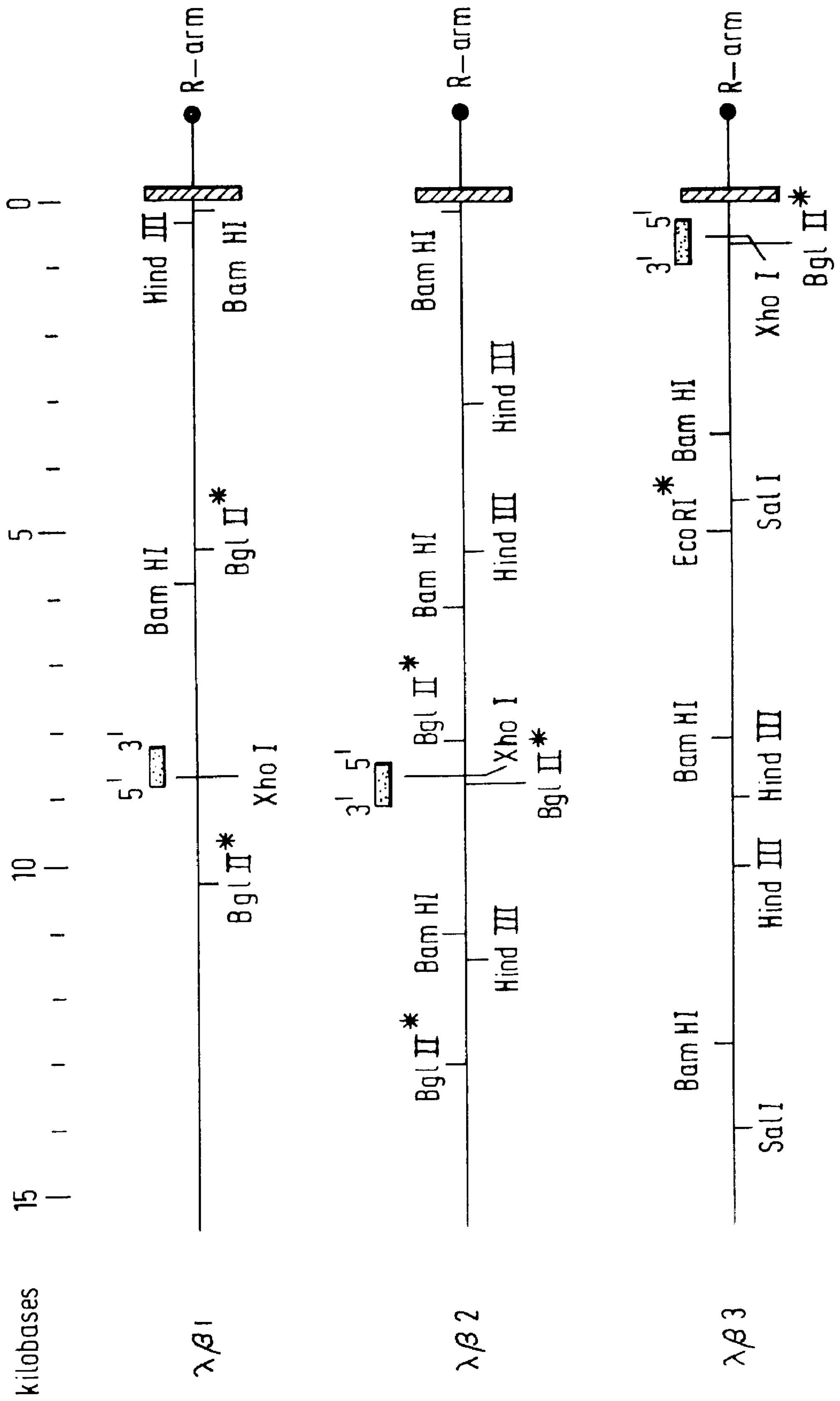
FIG. 7 shows a restriction map of the genomic bovine DNA inserts from three phage recombinants which hybridize the human fibroblast human interferon gene probe. The location and orientation of each BoIFN-β is indicated by the black rectangle. Restriction sites marked by an asterisk represent partial restriction mapping information.

Six of the phage recombinants which hybridized with the human IFN-β DNA probe were purified and their DNA isolated as described above for further analysis. Restriction mapping combined with Southern hybridization analysis indicated that the six isolates comprised three distinct regions of the bovine genome, thus implying a multigene BoIFN-β family. These results are summarized by the restriction maps shown in FIG. 7. To obtain a more detailed restriction map and nucleotide sequence for each distinct class of recombinant, hybridizing fragments were subcloned into plasmid vectors. Specifically, the 5kb BglII fragment of phage λβ1 and the 5 kb BamHI fragment of phage λβ2 were individually cloned into pBR322 at the BamHI site, the overlapping 4.5 kb EcoRI-XhoI and 1.4 kb PstI-HpaI fragment of phage λβ3 were inserted into pUC9 (deleted from the EcoRI-SalI sites) and pLeIF87 (10) (deleted from HpaI-PstI), respectively.

K. DNA Sequences of Three Distinct Bovine Fibroblast IFN Genes

Figure 8:
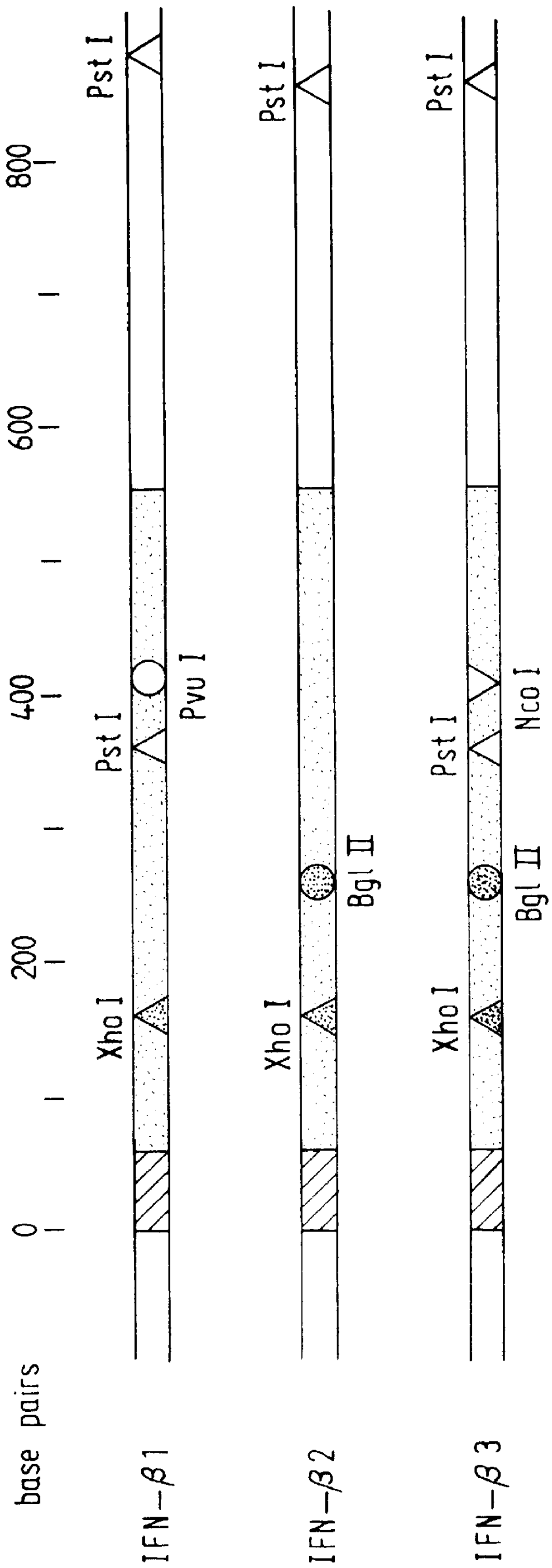
FIG. 8 shows a finer resolution restriction map for the three genes referenced in FIG. 7. Hatching represents the signal sequence; shading, the mature sequence.

FIG. 8 shows restriction maps for each of the three types of bovine IFN-β genes that were subcloned. These are easily distinguished by the presence of cleavage sites unique to each. The peptide coding regions as well as sequences immediately upstream and downstream for each gene was determined by the Maxam-Gilbert chemical procedure and are shown in FIGS. 9*a*, 9*b* and 9*c*. Nucleotide homology with the sequence determined for the human fibroblast interferon gene (12) predicts the correct reading frame and entire amino acid sequence for each bovine gene product, which includes a hydrophobic signal peptide of 21 amino acids followed by a mature protein of 185 residues. The bovine proteins are quite distinct from one another (Table 2, FIG. 10), but show an even greater difference (approximately 60 percent) with the human peptide.

Figure 11:
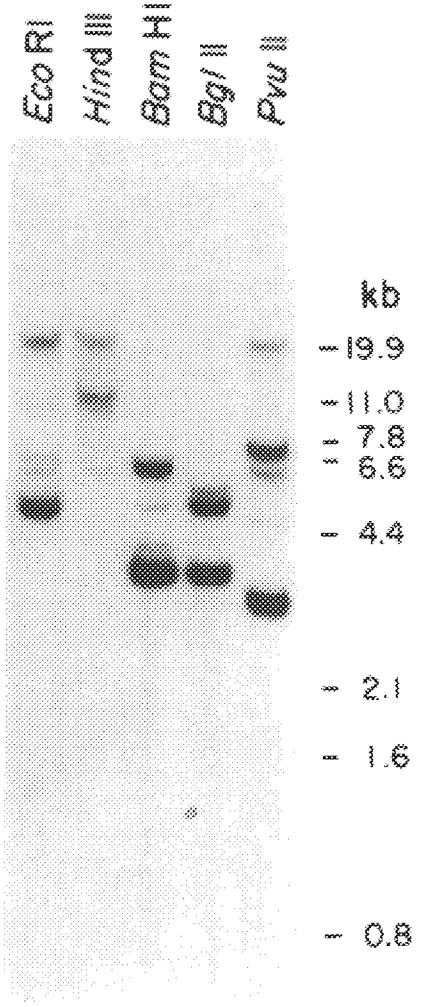
FIG. 11 is a Southern blot of FIG. 6 rehybridized with a BoIFN-β1 gene probe under conditions in which only a single hybridizing fragment would, in general, become apparent when performing an analogous experiment with human genomic DNA and the HuIFN-β gene (9).

The multigene nature of bovine fibroblast interferon was further demonstrated by rehybridizing the Southern blot shown in FIG. 11, with a radioactive probe prepared from a 415 bp EcoRI-PvuI fragment derived from pBoIFN-β1trp (described below). As seen in FIG. 11, this experiment provides evidence for the existence of additional, homologous IFN-β genes. The lesser hybridizing bands may in fact represent more distantly related genes, that would in turn encode more distinct β-IFNs.

TABLE 2

Pairwise Comparisons of Homology in Coding Sequences of Bovine IFN-βs and the Human IFN-β.

| | β1 | β2 | β3 | Huβ |
|---|---|---|---|---|
| β1 | | 138 (83) | 138 (83) | 84 (51) |
| β2 | 20 (95) | | 146 (88) | 92 (55) |
| β3 | 20 (95) | 19 (90) | | 87 (52) |
| Huβ | 16 (76) | 17 (81) | 16 (76) | |

The number of identical amino acids in each pair of coding sequences are shown. The 21 amino acid signal peptide are compared in the lower left part and the 166 amino acid mature IFN-βs are compared in the upper right part of the table. The total number of identical amino acids in each pair is listed first, followed by the percentage homology.

L. Direct Expression of Three Bovine IFN-βs in *E. coli*

Figure 12:
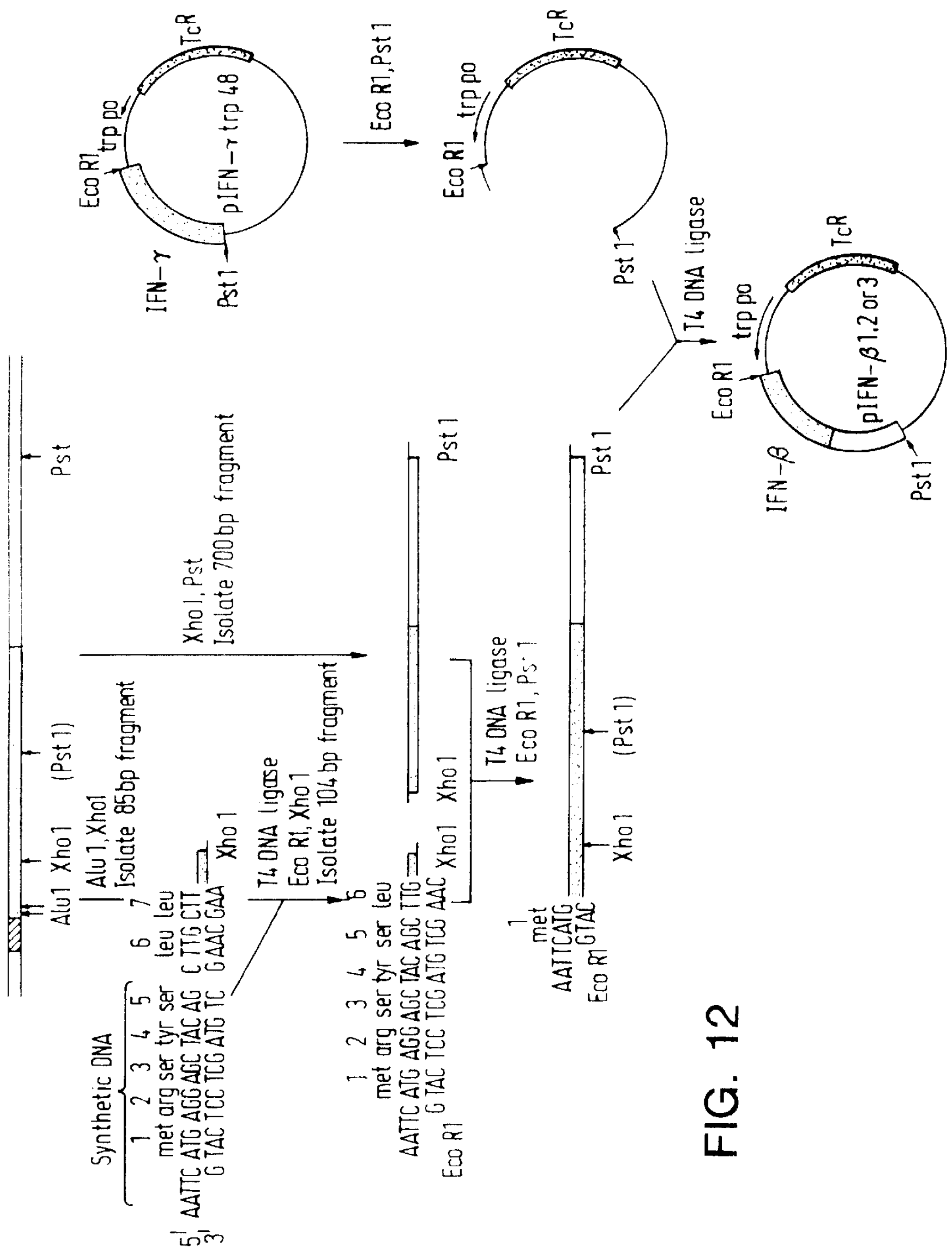
FIG. 12 schematically depicts the strategy used to express all three BoIFN-βs under control of the trp operon of *E. coli.*

As the three bovine IFN-β genes share many common DNA sequences and restriction sites (see FIG. 8), a general scheme is feasible for the expression of all three genes. Since the DNA sequence coding for the first five amino acids, which contains two AluI sites, was identical in each case, two complementary synthetic oligonucleotides were designed which incorporate an ATG n, restore the codons for the first 4 amino acids of mature bovine IFN-β, and create an EcoRI sticky for insertion after a trp promoter sequence. Construction of the expression plasmids is schematized in FIG. 12. Ligation of the synthetic oligomers to the 85 bp AluI-XhoI fragment derived from of the BoIFN-β subclone plasmids, followed by digestion with EcoRI and XhoI generates a 104 bp fragment flanked by EcoRI and XhoI sticky ends. The entire coding was then assembled into the trp expression vector by ligating the 104 bp fragment together with the approximately 700 bp XhoI-Pst fragment coding for the remainder of each BoIFN-β protein and the plasmid pIFN-γtr48-13 (55) from which the internal EcoRI-PstI fragment had been removed. The resulting plasmids, pBoIFN-β1trp, pBoIFN-β2trp and pBoIFN-β3trp all place the proper transcription and translation of the IFN-β genes under the control of the *E. coli* trp operon.

M. Characterization and Subcloning of Bovine Immune Interferon (BoIFN-γ) Gene

The ten phage recombinants that hybridized with the human IFN-γ probe were purified and DNA was prepared as described above. All ten DNA samples give specific hybridizing bands by Southern blot analysis. Clones λγ4 and λγ7 were chosen for further analysis, as they have distinct hybridizing band patterns. Restriction mapping of these two clones shows their DNA sequences overlap with each other. The overlapping region contains the restriction sites XbaI, EcoRV, and NcoI. DNA sequence analysis of these two clones shows an overall similar gene structure to the human immune interferon gene (70) and that λγ7 contains the sequence coding for the 4th exon and λγ4 contains sequences coding for the first three exons of bovine IFN-γ gene based on DNA sequence homology with the human IFN-γ gene. The amino acid sequence deduced for BoIFN-γ is compared with that of HuIFN-γ (55) and Murine IFN-γ, in FIG. 13.

To assemble the entire bovine IFN-γ gene on a continuous segment of DNA, the 3000 bp BamHI-NcoI fragment spanning the first three exons of bovine IFN-γ gene derived from λγ4 and the 2500 bp NcoI-Hind III fragment spanning the last exon derived from λγ7 were isolated. These two DNA fragments were then cloned into a BamHI-Hind III vector derived from pBR322 via a three part ligation.

N. Expression of Bovine IFN-γ Gene in Mammalian System

For purposes of obtaining an intron-less version of BoIFN-γ in order that this gene is expressible in a prokaryotic system such as *E. coli*, the gene was tailored for high level expression in an animal cell expression system to obtain significant quantities of specific mRNA. The 5500 bp BamHI-HindIII fragment spanning the entire bovine IFN-γ gene was inserted into a SV40 vector for expression in COS cells (44). Specifically, the BamHI-HindIII bovine IFN-γ gene fragment was cloned into a 2800 bp SV40 plasmid vector pDLΔR1 ((derived from the HBV antigen expression plasmid pHBs348-L by enzymatically deleting the EcoRI site upstream from the SV40 origin of replication selective to the direction of late transcription. Expression plasmid pHBs348-L was constructed by cloning the 1986 base-pair fragment resulting from EcoRI and BglII digestion of HBV (71) (which spans the gene encoding HBsAg) into the plasmid pML (72) at the EcoRI and BamHI sites. (pML is a derivative of pBR322 which has a deletion eliminating sequences which are inhibitory to plasmid replication in monkey cells (72)). The resulting plasmid (pRI-Bg1) was then linearized with EcoRI, and the 348 base-pair fragment representing the SV40 origin region was introduced into the EcoRI site of pRI-Bg1. The origin fragment can insert in either orientation. Since this fragment encodes both the early and late SV40 promoters in addition to the origin of replication, HBV genes could be expressed under the control of either promoter depending on this orientation (pHBs348-L representing HBs expressed under control of the late promoter)) between the BamHI and the Sal I site via a three part ligation in the presence of a 600 bp HindIII-SalI converter fragment derived from pBR322. Transfection of the resultant plasmid into COS cells leads to the efficient expression of bovine IFN-γ under the control of SV40 late promotor.

Poly A plus mRNA was prepared from transfected COS cells and used in turn to prepare cDNA by standard procedures (55). cDNA clones hybridizing with bovine IFN-γ gene probe were isolated. The cDNA clone with the longest Pst 1 insert was chosen for further analysis. DNA sequence analysis of this cDNA clone shows all the intron sequences predicted from the bovine IFN-γ genomic clone are correctly removed.

The cDNA was tailored for expression in *E. coli* by the primer repair method described above.

O. Rabbit and Porcine IFN-γ cDNA Isolation

The bovine IFN-γ cDNA was used as a hybridization probe to isolate the rabbit and porcine IFN-γ complementary DNA sequence. Rabbit and porcine RNA were isolated [Berger et al., *Biochemistry* 18, 5143 (1979)] from respective cultures of rabbit and porcine spleen cells induced with phytohemagglutinins (10 μg/ml) and phorbol 12-myristate 13-acetate (10 μg/ml) overnight. Individual samples of rabbit and porcine RNA were then run through oligo(dT)-cellulose to enrich for mRNA. Double stranded cDNA libraries from 2 μg samples of rabbit and porcine mRNA were used to prepare cDNA libraries in bacteriophage vector λgt10 (Huynh et al., *Practical Approaches in Biochemistry*, Grover ed., IRL, Oxford, England, 1985). 140 hybridizing clones (approx. 140) were obtained upon screening $1.5 \times 10^5$ phage recombinants from the rabbit cDNA library, whereas only 16 positive hybridizing clones were obtained upon screening $1.6 \times 10^6$ phage recombinants from the porcine cDNA library. DNA restriction mapping shows most of these λgt10 recombinant phages contain an EcoRI insert ranging in size from 1 kb to 1.5 kb. Two of the phages (λRγ7 and λRγ13) from the rabbit cDNA library and two (λPγ14 and λPγ16) from the porcine cDNA library were subcloned into M13mp19 [Norrander et al., *Gene* 26, 101 (1983)] and sequences by the dideoxy-chain method (62a).

The DNA nucleotide sequences of the longest rabbit IFN-γ cDNA clone (λRγ7) and of the porcine IFN-γ clone (λPγ14) and their predicted amino acid sequence based on DNA sequence homology with the human IFN-γ cDNA are shown on FIGS. 14*e* and 14*c* respectively. There is no nucleotide difference between the two individual rabbit IFN-γ cDNA clones sequenced except in the length of poly-As at the 3'-end. Similarly, the two individual porcine IFN-γ cDNA clones have identical DNA sequences except in the lengths of the 5'- and 3'-non-coding regions.

P. Amino Acid Sequence of IFN-γ

FIG. 15 presents the protein sequence homology of IFN-γ from several mammalian species. The signal sequences for human, bovine, porcine, and rabbit IFN-γ are 23 amino acids, while the mouse and rat signal sequences contain 22 amino acids due to a deletion at the 19th codon. The designation of the signal sequences of these animal IFN-γ's was based on structural homology with natural human IFN-γ. This stretch of amino acids contains features common to secretory protein signal sequences with a hydrophobic core of 10 amino acids extending from amino acids −7 to −16. The signal peptidase recognition sequence is expected to be (Cys/Ser)-Tyr-(Cys-Gly) corresponding to −21 to −23, with the cleavage site located after −23.

The polypeptide chains for mature human, bovine, and porcine IFN-γ have an identical length of 143 amino acids, while mature rabbit IFN-γ has 144 amino acids with an extra amino acid at the carboxy-terminal end. The mouse and rat IFN-γ have only 133 and 134 amino acids, respectively. Amino acid sequence comparisons show that the last 9 amino acid residues found in human, bovine and porcine IFN-γ have been deleted in mouse and rat IFN-γ. Additionally, amino acid residue 26 has been deleted in mouse IFN-γ. Apart from mouse and rat IFN-γ with a cysteine at the C-terminal end, which may not be present in vivo, none of the other mature IFN-γs described here contain any cysteines. Disulfide linkage is therefore not required to maintain the overall structure of mature IFN-γ, although full length recombinant murine IFN-γ readily builds an intra dimer disulfide bridge (which does not change the specific activity). Rabbit IFN-γ contains three potential N-glycosylation sequences Asn-X-(Thr/Ser) [Struck et al., *J Biol Chem* 253, 5786 (1978)], whereas the other five IFN-γs have only two in their mature proteins. Mouse IFN-γ is the only IFN-γ with an additional glycosylation site within its signal peptide. The position of these sites is apparently not conserved among the various IFN-γs.

The overall amino acid sequence homology among human, bovine, porcine and rabbit IFN-γ is above 60 percent with respect to one another, whereas the homology between either mouse or rat IFN-γ and any of the other four IFN-γs presented here is less than 40 percent. The homology between mouse and rat IFN-γ exceeds 85 percent.

Q. Synthesis of Bovine, Porcine, and Rabbit IFN-γ in *E. coli*

The procedure used to express the cDNA inserts of bovine porcine and rabbit IFN-γ directly in *E. coli* was as follows: Using synthetic oligonucleotides, an ATG codon for the initiator methionine was introduced in front of the Gln codon for the presumed amino-terminus of mature bovine, porcine and rabbit IFN-γ. This ATG initiation codon was in turn preceded by XbaI sticky ends. Portable restriction fragments containing the entire mature coding sequence for IFN-γ were generated by cleavage with XbaI and a second restriction enzyme with a unique cleavage site located at the 3'-non-coding region of each IFN-γ cDNA clone; namely, DraI for bovine IFN-γ cDNA, SspI for porcine IFN-γ cDNA, and NsiI for rabbit IFN-γ cDNA. The resulting restriction fragments were inserted between the XbaI and Pst site of the trp expression plasmid pIFN-β3 (see supra.), of which the XbaI site is located immediately downstream of the trp leader ribosome binding site.

High level expression of bovine, porcine, and rabbit IFN-γ were obtained due to transcription from the strong trp promoter and to the placement of the ribosome binding sequence of the trp leader at an optimal distance from the ATG initiator codon of the inserted coding sequence for efficient translation. Analysis of bacterial extracts harboring the bovine, porcine, and rabbit IFN-γ expression plasmids by SDS-gel electrophoresis shows the presence of IFN-γ as a major band on the protein gel with an apparent molecular weight of 17 to 18k dalton.

These IFN-γ were purified to homogeneity from *E. coli* cell extracts by a combination of adsorption, ion-exchange and size exclusion chromatography. Purified proteins were routinely stored at 4° C. at concentrations ranging from 0.5–5.0 mg/ml in 20 mM Tris-HCl, 0.5M NaCl pH 8.0 after sterile filtration. Protein concentrations were determined using a Bradford-type dye binding assay employing bovine serum albumin as a standard. These IFN-γ are all judged to have a purity of >98 percent based on SDS PAGE with both Coomassie and silver stain. Endotoxin levels in all these preparations are below 0.1 ng/mg (<1 EU/mg). Size exclusion chromatography on a Pharmacia Superose 12 column under non-denaturing conditions suggests that rBoIFN-γ, rPoIFN-γ, and rRbIFN-γ exist as dimers in solution with apparent molecular weights of 25.8K, 31.6K, and 21.0K, respectively. In 4M guanidine hydrochloride, however, they chromatograph as monomers. These values fit well with the apparent molecular weights found by SDS PAGE. All three species still carry the initiator methionine (from direct expression) on their N-terminus.

R. Estimation of the Number of IFN-γ in the Bovine, Porcine, and Rabbit Genomes

The number of IFN-γ genes in the various mammalian genomes was estimated by Southern blot analysis. Bovine, porcine, and rabbit chromosomal DNA were digested with several restriction enzymes, fractionated by agarose gel electrophoresis, and transferred to nitrocellulose. Hybridization was performed under either stringent or non-stringent conditions with a radiolabeled 600 bp AvaII fragment derived from the bovine IFN-γ cDNA clone. The presence of only one or two hybridizing bands upon digestion with various restriction enzymes indicates the existence of just one copy of IFN-γ gene per haploid genome. Bovine, porcine, rabbit, human and mouse IFN-γ are therefore all single copy genes.

S. Construction of Bacterial Plasmid for the Expression of Porcine IFN-α1

Two synthetic nucleotides

```
         M  C  D  L  P
5'-AATTCATGTGCGACCTGCC
        GTACACGCTGGACGGACT-5'
```

were designed that incorporate an ATG translation initiation codon, restore the codons for the first four amino acids of mature porcine IFN-α1 and create an EcoRI and Dde I sticky ends. Ligation of these oligomers to the 150 bp partial Dde-I-NcoI fragment and the 550 bp NcoI-AhaIII fragment derived from the porcine IFN-α1 genomic clone generates a 720 bp synthetic-natural gene that codes for mature porcine IFN-α1 bounded by EcoRI and AhaIII sites. Insertion of this porcine IFN-α1 gene flanked by EcoRI and AhaIII ends into the plasmid pIFN-β3 (Leung et al., *Bio/Technology* 2, 458 (1984)) between the EcoRI and PstI sites yields the expression plasmid pTrpPoA1 in which the porcine α1 gene is transcribed under the control of the *E. coli* trp operon.

T. Preparation of Bacterial Extracts overnight cultures grown in LB broth containing either 0.02 mg/ml of ampicillin or 0.005 mg/ml tetracycline were inoculated at a 1:100 dilution into 50 ml of M9 medium (63) containing 0.2 percent glucose, 0.5 percent casamino acids and the appropriate drug, and grown at 37° C. with shaking to an A550=1.0. Ten ml samples were harvested by centrifugation and immediately quick-frozen in a dry ice-ethanol bath. The frozen pellets were resuspended in 1 ml of 7M guanidine, incubated on ice for 5 minutes, and diluted into PBS for assay. Alternatively, the frozen pellets were lysed by the addition of 0.2 ml of 20 percent sucrose, 100 mM Tris-HCl (pH 8.0), 20 mM EDTA and 5 mg/ml lysozyme. After 20 minutes on ice, 0.8 ml of 0.3 percent Triton X-100, 0.15M Tris-HCl (pH 8.0), 0.2M EDTA and 0.1 mM PMSF was added. The lysate was cleared by centrifugation at 19,000 rpm for 15 minutes and the supernatant assayed after dilution into PBS.

U. Interferon Assays

Bovine interferon activity was assayed by a cytopathic effect (CPE) inhibition assay performed in 96 well microtiter plates as follows:

1. Add to each well of a 96 well microliter plate (8 rows×12 columns) 100 μl of a suspension of cells in media containing 10 percent fetal calf serum. Cell concentration is adjusted to give confluent monolayer the next day.
2. Rock plates gently on a rocker platform for 10 minutes to evenly distribute cells.

Next Day

3. Add to each well in the first column 80 μl of additional media.
4. Add to a well in the first column, 20 μl of a sample to be assayed for interferon activity.
5. Mix the sample and medium in the well by withdrawing and ejecting 100 μl of the contents of the well several times with a 100 μl pipette.
6. Transfer 100 μl of the contents of a well in the first column horizontally to a well in second column.
7. Mix as in step 3.
8. Continue to transfer 100 μl of the contents of a well from column to subsequent column until a total of 11 transfers are performed.
9. Remove and discard 100 μl of the contents of the well in the 12th column. This procedure produces a serial set of two-fold dilutions.
10. Each assay plate includes appropriate NIH standards.
11. Incubate plates in a $CO_2$ incubation, 37° C. for 24 hours.
12. Each assay plate contains wells which receive 100 μl of cell suspension and 100 μl of medium to serve as cell growth controls and wells which receive 100 μl cell suspension, 100 μl of medium and 50 μl of virus suspension to serve as virus-induced cytopathogenic controls.
13. Challenge all wells except cell controls with 50 μl of a virus suspension. Multiplicity of infection used is that amount of virus which causes 100 percent cytopathic effect on the particular cell line within 24 hours.
14. Reincubate plates for 24 hours at 37° C. in $CO_2$ incubation.
15. Remove fluid from plates and stain cells with 0.5 percent crystal violet. Allow cells to stain for 2–5 minutes.
16. Rinse plate well in tap water and allow to dry.
17. Titer of Interferon on sample is the reciprocal of the dilution where 50 percent viable cells remain.
18. The activity of all samples are normalized by the Reference Units Conversion Factor which is calculated from:

Actual Titer of NIH Standard Reference Units

Observed Titer in Assay=Conversion Factor. (See 69). Extracts prepared from *E. coli* strain 294 (ATCC No. 31446) transformed with pBoIFN-α1trp55 showed significant activity on a bovine kidney cell line (MDBK) challenged with VS virus (Indiana strain), but not on monkey kidney (VERO), human cervical carcinoma (HeLa), rabbit kidney (Rk-13) or mouse (L929) cell lines challenged in a similar fashion. Control extracts prepared from strain 294 transformed with pBR322 did not exhibit activity on MDBK cells. Table 3 summarizes the in vitro antiviral activity BoIFN-α1 on various challenged animal and human cell lines. BoIFN-α1 is readily distinguished from the human leukocyte IFN's by an apparent lack of antiviral activity on human cells relative to its activity on bovine cells employing VS virus as the challenge. Table 4 shows the level of interferon activity obtained in extracts prepared from *E. coli* W3110 which has been transformed with the expression plasmids pBoIFN-α4trp15, pBoIFN-β1trp, pBoIFN-β2trp and pBoIFN-β3trp. Particularly significant is the observation that the bovine fibroblast interferons are approximately 30-fold more active on a bovine kidney cell line than on a human amnion cell line, whereas the reciprocal relationship is found for human fibroblast IFN (12).

TABLE 3

| Cell Line | IFN Preparation | Titer (units/ml) VSV | EMCV |
|---|---|---|---|
| MDBK | LeIF A Standard | 640 | NA |
| | Bovine leukocyte IFN | 300,000 | NA |
| | Control Extract | <40 | NA |
| HeLa | LeIF A Standard | 650 | 1,500 |
| | Bovine leukocyte IFN | <40 | <23 |
| | Control Extract | <40 | <23 |
| L-929 | Mouse IFN Standard | 640 | 1,000 |
| | Bovine leukocyte IFN | <20 | <31 |
| | Control Extract | <20 | <31 |
| RK-13 | Rabbit IFN Standard | 1,000 | NA |
| | Bovine leukocyte IFN | <60 | NA |
| | Control Extract | <60 | NA |
| VERO | LeIF A Standard | | 1,500 |
| | Bovine leukocyte IFN | | <12 |
| | Control Extract | | <12 |

MDBK = bovine kidney cells
VERO = African Green monkey kidney cells
HeLa = human cervical carcinoma cells
RK-12 = rabbit kidney cells
NA = not application as virus does not replicate well in respective cell.

TABLE 4

Interferon Activity in Extracts of *E. coli*

| *E. coli* 294 transformed by: | IFN-β activity (units/liter culture) MDBK-VSV | IFN-β activity (units/liter culture) WISH-VSV |
|---|---|---|
| pIFN-α1 | $1.0 \times 10^8$ | N.D. |
| pIFN-β1 | $2.2 \times 10^8$ | $6.5 \times 10^6$ |
| pIFN-β2 | $1.1 \times 10^8$ | $3.5 \times 10^6$ |
| pIFN-β3 | $6.0 \times 10^8$ | $2.0 \times 10^7$ |

Bacterial extracts were prepared and assayed for interferon activity using the bovine kidney MDBK cell line and the human amnion WISH cell line and VSV as challenge according to a published procedure (Weck et al., 1981)

Similarly, bioassay results demonstrated that activity was present as follows:

TABLE 5

| Interferon | Cell Line | Activity in *E. coli* Extant |
|---|---|---|
| porcine IFN-α1 | MDBK | $2.5 \times 10^{10}$ U/L<br>$8.33 \times 10^5$ U/ml/OD |
| porcine IFN-γ | PK-15 | $1.2 \times 10^{10}$ U/L<br>$3 \times 10^5$ U/ml/OD |
| rabbit IFN-γ | RK-13 | $1.58 \times 10^8$ U/L<br>$8 \times 10^4$ U/ml/OD |

Administrable Compositions

The compounds of the present invention can be formulated according to known methods to prepare useful compositions, whereby the non-human animal interferon products hereof are combined in admixture with (an) acceptable carrier vehicle(s). Suitable vehicles and their formulation have been described. Such compositions will contain an effective amount of the interferon protein hereof together with a suitable amount of vehicle in order to prepare acceptable compositions suitable for effective administration, via known routes, e.g., parenteral, to the host.

It will be understood that the non-human animal interferons embraced herein exist with natural allelic variations. These variations may be demonstrated by (an) amino acid difference(s) in the overall sequence or by deletions, substitutions, insertions, inversions or additions of (an) amino acid(s) in said sequence. All such allelic variations are included within the scope of this invention. In addition, so long as the essential biological activity of a given non-human animal interferon hereof is manifest in kind, other variations or derivations of the natural sequences are included herein. These can be prepared by induced mutagenesis of the underlying DNA sequence, for example.

Notwithstanding that reference has been made to particular preferred embodiments, it will be further understood that the present invention is not to be construed as limited to such, rather to the lawful scope of the appended claims.

Bibliography

1. Rinaldo et al., *Infection and Immunity* 14, 660 (1976).
2. Fulton and Rosenquist, *Am. J. Vet. Res.* 37, 1497 (1976).
3. Babrick and Rouse, *Infection and Immunity* 13, 1567 (1976).
4. Todd et al., *Infection and Immunity* 5, 699 (1972).
5. Ahl and Rump, *Infection and Immunity* 14, 603 (1976).
6. Babrick and Rouse, *Intervirology* 8, 250 (1977).
7. Tovey et al., *J. Gen. Virol.* 36, 341 (1977).
8. Goeddel et al., *Nature* 287, 411 (1980).
9. Goeddel et al., *Nature* 290, 20 (1981).
10. Yelverton et al., *Nucleic Acids Research* 9, 731 (1981).
11. Gutterman et al., *Annals of Int. Med.* 93, 399 (1980).
12. Goeddel et al., *Nucleic Acids Research* 8, 4057 (1980).
13. Yip et al., *Proc. Natl. Acad. Sci.* (*USA*) 78, 1601 (1981).
14. Taniguchi et al., *Proc. Natl. Acad. Sci.* (*USA*) 78, 3469 (1981).
15. Bloom, *Nature* 289, 593 (1980).
16. Sonnenfeld et al., *Cellular Immunol.* 40, 285 (1978).
17. Fleishmann et al., *Infection and Immunity* 26, 248 (1979).
18. Blalock et al., *Cellular Immunol.* 49, 390 (1980).
19. Rudin et al., *Proc. Natl. Acad. Sci.* (*USA*) 77, 5928 (1980).
20. Crane et al., *J. Natl. Cancer Inst.* 61, 871 (1978).
21. British Patent Publication No. 2007672A.
22. Wetael, *American Scientist* 68, 664 (1980).
23. *Microbiology,* 2nd Edition, Harper and Row Publishers, Inc., Hagerstown, Md. (1973), esp. pp. 1122 et seq.
24. *Scientific American* 245, 66 et seq. (1981).
25. British Patent Publication No. 2055382A.
26. German Offenlegungsschrift 2644432.
26a. Leder et al., *Science* 16, 175 (1977).
27. Chang et al., *Nature* 275, 617 (1978).
28. Itakura et al., *Science* 198, 1056 (1977).
29. European Patent Publication No. 0036776.
30. Siebenlist et al., *Cell* 20, 269 (1980).
31. Stinchcomb et al., *Nature* 282, 39 (1979).
32. Kingsman et al., *Gene* 7, 141 (1979).
33. Tschumper et al., *Gene* 10, 157 (1980).
34. Mortimer et al., *Microbiological Reviews* 44, 519 (198).
35. Miozzari et al., *Journal of Bacteriology* 134, 48 (1978).
36. Jones, *Genetics* 85, 23 (1977).
37. Hitzeman et al., *J. Biol. Chem.* 255, 12073 (1980).
38. Hess et al., *J. Adv. Enzyme Regul.* 7, 149 (1968).
39. Holland et al., *Biochemistry* 17, 4900 (1978).
40. Bostian et al., *Proc. Natl. Acad. Sci.* (*USA*) 77, 4504 (1980).
41. *The Molecular Biology of Yeast* (Aug 11–18, 1981), Cold Spring Harbor-Laboratory, Cold Spring Harbor, N.Y.
42. Chambon, *Ann. Rev. Biochemistry* 44, 613 (1975).
43. *Tissue Culture*, Academic Press, Kruse and Patterson, eds. (1973).
44. Gluzman, *Cell* 23, 175 (1981).

45. Goeddel et al., *Nature* 281, 544 (1979).
46. Lusky et al., *Nature* 293, 79 (1981).
47. Gluzman et al., Cold Spring Harbor Symp. Quant. Biol. 44, 293 (1980).
48. Fiers et al., *Nature* 273, 113 (1978).
49. Reddy et al., *Science* 200, 494 (1978).
50. Blin and Stafford, *Nucleic Acids Research* 3, 2303 (1976).
51. Maniatis et al., *Cell* 15, 687 (1978).
51a. Blattner et al., *Science* 196, 161 (1977).
52. Rimm et al., *Gene* 12, 301 (1980).
53. Blattner et al., (1978) Procedures for Use of Charon Phages in Recombinant DNA Research, Research Resources Branch, National Institute of Allergy and Infectious Diseases, Bethesda, Md.
54. Blattner et al., *Science* 202, 1279 (1978).
55. Gray et al., *Nature* 295, 503 (1982).
56. Souther, *J. Mol. Biol.* 98, 503 (1975).
57. Weck et al., *Nucleic Acids Research* 9, 6153 (1981).
58. Taylor et al., *Biochem. Biophys. Acta* 442, 324 (1976).
59. Denhardt, *Biochem. Biophys. Res. Comm.* 23, 641 (1966).
60. Wahl et al., *Proc. Natl. Acad. Sci.* 76, 3683 (1979).
61. Nagata et al., *Nature* 287, 401 (1980).
62. Benton and Davis, *Science* 196, 180 (1977).
62a. Messing et al., *Nucleic Acids Research* 9, 309 (1981).
63. Miller (1972) Experiments in Molecular Genetics, Cold Spring Harbor Laboratory, Cold Spring Harbor, N.Y.
64. Birnboim et al., *Nucleic Acids Research* 7, 1513 (1979).
65. Maxam and Gilbert, *Proc. Natl. Acad. Sci.* 74, 560 (1977).
66. McGrath and Levinson, *Nature* 295, 423 (1982).
67. Itakura et al., *Science* 198, 1056 (1977).
68. Crea et al., *Proc. Natl. Acad. Sci.* 75, 5765 (1978).
69. Stewart (1979) *The Interferon System*, Springer-Verlag, New York, pp. 17 et seq.
70. Gray and Goeddel, *Nature* 298, 859 (1982).
71. *Animal Virus Genetics* (Ed. Fields et al.), Chapter 5, p. 57, Academic Press, New York, (1980).
72. Lusky and Botchan, *Nature* 293, 79 (1981).

We claim:

1. An essentially purified and isolated nucleic acid molecule comprising a nucleotide sequence selected from the group consisting of:

the mature bovine interferon alpha-1 coding sequence of FIGS. 3A-1–3A-2;

the mature bovine interferon alpha-2 coding sequence of FIGS. 3B-1–3B-2;

the mature bovine interferon alpha-3 coding sequence of FIGS. 3C-1–3C-2;

the mature bovine interferon alpha-4 coding sequence of FIGS. 3D-1–3D-2;

the mature bovine interferon beta-1 coding sequence of FIGS. 9A-1–9A-2;

the mature bovine interferon beta-2 coding sequence of FIGS. 9B-1–9B-2;

the mature bovine interferon beta-3 coding sequence of FIGS. 9C-1–9C-2;

the mature porcine interferon alpha-1 coding sequence of FIG. 14A;

the mature porcine interferon beta-1 coding sequence of FIG. 14B;

the mature porcine interferon gamma coding sequence of FIG. 14C;

the mature feline interferon beta-1 coding sequence of FIG. 14D; and the mature laprine interferon gamma coding sequence of FIG. 14E.

2. A nucleic acid molecule according to claim 1 comprising the complete interferon propeptide coding sequence, including the signal peptide-encoding sequence, as shown in the respective figure(s).

3. A nucleic acid molecule according to claim 1 comprising the complete cDNA sequence shown in the respective figure(s).

4. A replicable expression vehicle comprising the nucleic acid molecule of claim 1 and capable, in a transformant microorganism or cell culture, of expressing the nucleic acid sequence encoding the polypeptide.

5. A microorganism or cell culture transfected with the replicable expression vehicle according to claim 4.

6. An essentially purified and isolated nucleic acid molecule comprising a nucleic acid sequence encoding a polypeptide comprising the sequence of a non-human animal interferon having an amino acid sequence selected from the group consisting of:

the mature bovine interferon alpha-1 amino acid sequence set forth in FIGS. 3A-1–3A-2;

the mature bovine interferon alpha-2 amino acid sequence set forth in FIGS. 3B-1–3B-2;

the mature bovine interferon alpha-3 amino acid sequence set forth in FIGS. 3C-1–3C-2;

the mature bovine interferon alpha-4 amino acid sequence set forth in FIGS. 3D-1–3D-2;

the mature bovine interferon beta-1 amino acid sequence set forth in FIGS. 9A-1–9A-2;

the mature bovine interferon beta-2 amino acid sequence set forth in FIGS. 9B-1–9B-2;

the mature bovine interferon beta-3 amino acid sequence set forth in FIGS. 9C-1–9C-2;

the amino acid sequence of mature bovine interferon-gamma set forth in FIG. 13;

the amino acid sequence of mature murine interferon-gamma set forth in FIG. 13;

the mature porcine interferon alpha-1 amino acid sequence set forth in FIG. 14A;

the mature porcine interferon beta-1 amino acid sequence set forth in FIG. 14B;

the mature porcine interferon gamma amino acid sequence set forth in FIG. 14C;

the mature feline interferon beta-1 amino acid sequence set forth in FIG. 14D;

the mature laprine interferon-gamma amino acid sequence set forth in FIG. **14*e*; and the amino acid sequence of mature rat interferon-gamma set forth in FIG. 14E**.

7. The nucleic acid molecule according to claim 6, wherein the nucleic acid sequence additionally comprises a sequence encoding the amino acid methionine attached to the N-terminus of the interferon.

8. The nucleic acid molecule according to claim 6, wherein the nucleic acid sequence additionally comprises a sequence encoding a cleaveable conjugate or signal protein attached to the N-terminus of the interferon.

9. A nucleic acid molecule according to claim 6 comprising a sequence encoding the complete interferon propeptide sequence, including the signal peptide sequence, as shown in the respective figure(s).

10. The nucleic acid molecule of claim 6 wherein the polypeptide comprises a bovine alpha interferon having an amino acid sequence selected from the group consisting of the amino acid sequence of amino acids 1 to 166 of FIGS. 3A-1–A-2, the amino acid sequence of amino acids 1 to 166 of FIGS. 3B-1–B-2, the amino acid sequence of amino acids 1 to 166 of FIGS. 3C-1–C-2, and the amino acid sequence of amino acids 1 to 172 of FIGS. 3D-1–D-2.

11. The nucleic acid molecule of claim 6 wherein the polypeptide comprises a bovine beta interferon having an amino acid sequence selected from the group consisting of the amino acid sequence of amino acids 1 to 165 of FIGS. 9A-1–A-2, the amino acid sequence of amino acids 1 to 165 of FIGS. 9B-1–B-2, and the amino acid sequence of amino acids 1 to 165 of FIGS. 9C-1–C-2.

12. The nucleic acid molecule of claim 6 wherein the polypeptide comprises the bovine gamma interferon amino acid sequence of FIG. 13.

13. The nucleic acid molecule of claim 6 wherein the polypeptide comprises a porcine interferon having an amino acid sequence selected from the group consisting of the amino acid sequence of amino acids 1 to 166 of FIG. 14A, the amino acid sequence of amino acids 1 to 164 of FIG. 14B, and the amino acid sequence of amino acids 1 to 143 of FIG. 14C.

14. The nucleic acid molecule according to claim 6, wherein the nucleic acid sequence is operably linked with a control sequence capable of effecting expression of the nucleic acid sequence encoding the polypeptide in a microorganism or cell culture transfected with the nucleic acid molecule.

15. A replicable expression vehicle comprising the nucleic acid molecule of claim 14 and capable, in a transformant microorganism or cell culture, of expressing the nucleic acid sequence encoding the polypeptide.

16. A process for producing a polypeptide comprising the amino acid sequence of a non-human animal interferon comprising causing a culture of a microorganism or cell culture, transformed with a replicable expression vehicle according to claim 14, to grow and effect production of the polypeptide and recovering the polypeptide.

17. A process of producing an expression vehicle according to claim 15 comprising constructing a DNA molecule comprising a first DNA sequence coding for the polypeptide operably linked to a second DNA sequence capable of effecting expression of the first DNA sequence in a microorganism or cell culture transfected with the expression vehicle.

18. A microorganism or cell culture transfected with the nucleic acid molecule according to claim 14.

19. The microorganism according to claim 18 that is a transfected *E. coli* strain.

20. The microorganism or cell culture according to claim 18 that is capable of producing the polypeptide in a form where the amino acid sequence of the non-human animal interferon is unaccompanied by the signal peptide or presequence peptide of the non-human animal interferon.

21. A process which comprises expressing in the microorganism or cell culture according to claim 20 the nucleic acid sequence encoding the polypeptide in a form where the amino acid sequence of the non-human animal interferon is unaccompanied by the signal peptide or presequence peptide of the non-human animal interferon.

* * * * *